(12) United States Patent
Kucenas et al.

(10) Patent No.: US 11,413,324 B2
(45) Date of Patent: Aug. 16, 2022

(54) COMPOSITIONS AND METHODS FOR TREATING PERIPHERAL NERVE DISEASE, DISORDERS, AND INJURIES

(71) Applicant: University of Virginia Patent Foundation, Charlottesville, VA (US)

(72) Inventors: Sarah Kucenas, Charlottesville, VA (US); Taylor Welsh, Staunton, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/495,064

(22) PCT Filed: Mar. 16, 2018

(86) PCT No.: PCT/US2018/022797
§ 371 (c)(1),
(2) Date: Sep. 17, 2019

(87) PCT Pub. No.: WO2018/170359
PCT Pub. Date: Sep. 20, 2018

(65) Prior Publication Data
US 2020/0390852 A1    Dec. 17, 2020

Related U.S. Application Data

(60) Provisional application No. 62/472,726, filed on Mar. 17, 2017.

(51) Int. Cl.
| | | |
|---|---|---|
| *A61P 25/28* | (2006.01) | |
| *A61K 31/519* | (2006.01) | |
| *A61K 38/16* | (2006.01) | |
| *A61K 31/138* | (2006.01) | |
| *A61K 31/145* | (2006.01) | |
| *A61K 31/196* | (2006.01) | |
| *A61K 31/215* | (2006.01) | |
| *A61K 31/365* | (2006.01) | |
| *A61K 31/426* | (2006.01) | |
| *A61K 38/17* | (2006.01) | |

(52) U.S. Cl.
CPC ......... *A61K 38/164* (2013.01); *A61K 31/138* (2013.01); *A61K 31/145* (2013.01); *A61K 31/196* (2013.01); *A61K 31/215* (2013.01); *A61K 31/365* (2013.01); *A61K 31/426* (2013.01); *A61K 31/519* (2013.01); *A61K 38/1787* (2013.01); *A61P 25/28* (2018.01)

(58) Field of Classification Search
CPC .............................. A61K 31/519; A61P 25/28
See application file for complete search history.

(56) References Cited

U.S. PATENT DOCUMENTS

| | | | | |
|---|---|---|---|---|
| 7,160,899 B2 * | 1/2007 | Peters | .................. | C07K 14/475 514/307 |
| 2011/0262442 A1 * | 10/2011 | Hamilton | ................ | A61P 25/28 424/139.1 |

FOREIGN PATENT DOCUMENTS

WO    WO 2011/123798 A2    10/2011

OTHER PUBLICATIONS

Ghai et al. The Journal of Pharmacology and Experimental Therapeutics, 1987, vol. 242, No. 3, pp. 784-790 (Year: 1987).*
Howell et al. The Journal of Pharmacology and Experimental Therapeutics, 1993, vol. 267, No. 1, pp. 432-439 (Year: 1993).*
Paterniti et al. Journal of Neuroinflammation, 2011, 8:31, 14 pages (Year: 2011).*
Bergles et al. (2000). Glutamatergic synapses on oligodendrocyte precursor cells in the hippocampus. Nature 405, 187-191.
Chen et al. (1999). A(2A) adenosine receptor deficiency attenuates brain injury induced by transient focal ischemia in mice. J Neurosci 19, 9192-9200.
Dubois-Dalcq et al. "From fish to man: understanding endogenous remyelination in central nervous system demyelinating diseases" Brain. May 12, 2008 (May 12, 2008) vol. 131 , p. 1686-1700.
Emery & Lu (2015). Transcriptional and epigenetic regulation of oligodendrocyte development and myelination in the central nervous system. Cold Spring Harb Perspect Biol 7, a020461.
Golder et al. (2008). Spinal Adenosine A2a Receptor Activation Elicits Long-Lasting Phrenic Motor Facilitation. J Neurosci 28, 2033-2042.
International Preliminary Report on Patentability corresponding to International Application No. PCT/US2018/022797 dated Sep. 17, 2019.
International Search Report for PCT/US2018/022797 dated Jun. 11, 2018.
Luyt et al. "Developing oligodendrocytes express functional GABAB receptors that stimulate cell proliferation and migration" Journal of Neurochemistry. Mar. 2007. vol. 100, p. 822-840.
Rebola et al. (2008). Adenosine A2A receptors are essential for long-term potentiation of NMDA-EPSCs at hippocampal mossy fiber synapses. Neuron 57, 121-134.

(Continued)

*Primary Examiner* — James D. Anderson
(74) *Attorney, Agent, or Firm* — Jenkins, Wilson, Taylor & Hunt, P.A.

(57) ABSTRACT

During development, OPCs migrate extensively throughout the spinal cord, but their migration is restricted at transition zones (TZ). At these specialized locations, unique glial cells in both zebrafish and mice are at least partially responsible for preventing peripheral OPC migration, but the mechanisms of this regulation are not understood. In order to elucidate the signals that mediate OPC segregation at motor exit point (MEP) TZs, we performed an unbiased small molecule screen. Using chemical screening and in vivo imaging, we discovered that inhibition of A2a adenosine receptors (AR) causes ectopic OPC migration out of the spinal cord. In our studies, we provide in vivo evidence that endogenous neuromodulation by adenosine regulates OPC migration along motor axons, specifically at the MEP TZ. This work opens exciting possibilities for understanding how OPCs reach their final destinations during development and identifies mechanisms that could promote their migration in disease.

9 Claims, 19 Drawing Sheets

(56) References Cited

OTHER PUBLICATIONS

Wei et al. (2013) Blocking A2B adenosine receptor alleviates pathogenesis of experimental autoimmune encephalomyelitis via inhibition of IL-6 production and Th17 differentiation. J Immunol 190, 138-146.
Written Opinion of the International Searching Authority for PCT/US2018/022797 dated Jun. 11, 2018.
Boehmler et al. (2009). Identification of zebrafish A2 adenosine receptors and expression in developing embryos. Gene Expr Patterns 9, 144-151.
De Lera Ruiz et al. (2014). Adenosine A2A receptor as a drug discovery target. J Med Chem 57, 3623-3650.
Jarvis & Williams (1989). Direct autoradiographic localization of adenosine A2 receptors in the rat brain using the A2-selective agonist,[3H] CGS 21680. Eur J Pharmacol 168, 243-246.
Jiang et al. (1996). 6-phenyl-1,4-dihydropyridine derivatives as potent and selective A3 adenosine receptor antagonists. J. Med. Chem. 39, 4667-4675.
Ongini et al. (1999). Comparison of CGS 15943, ZM 241385 and SCH 58261 as antagonists at human adenosine receptors. Naunyn-Schmiedeberg's Arch Pharmacol 359, 7-10.
Othman et al. (2003). Oligodendrocytes express functional A1 adenosine receptors that stimulate cellular migration. Glia 44, 166-172.
Sebastiao & Ribeiro (2015). Neuromodulation and metamodulation by adenosine: impact and subtleties upon synaptic plasticity regulation. Brain Res 1621, 102-113.

* cited by examiner

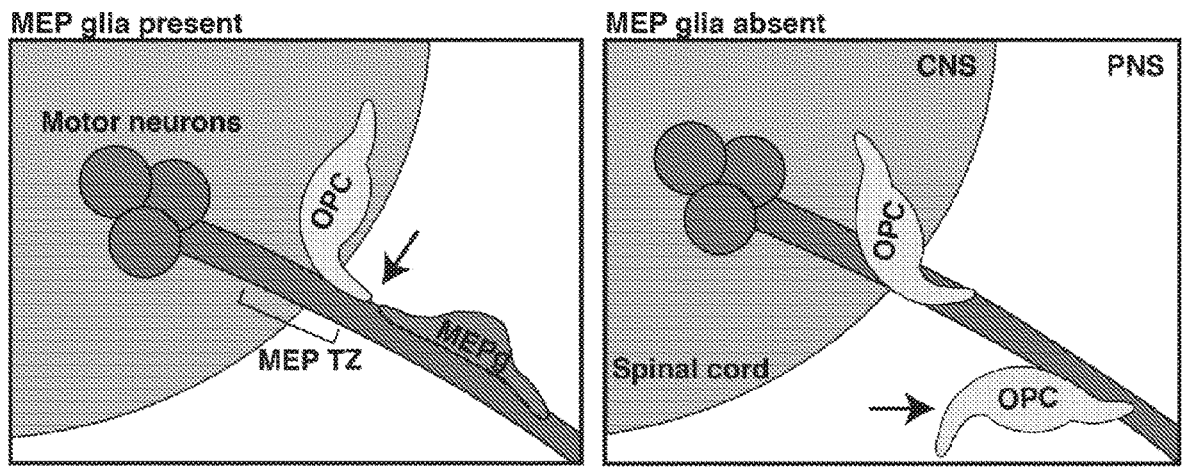
FIG. 1A
FIG. 1B
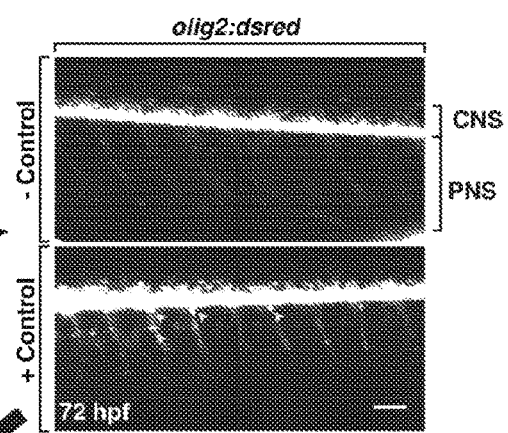
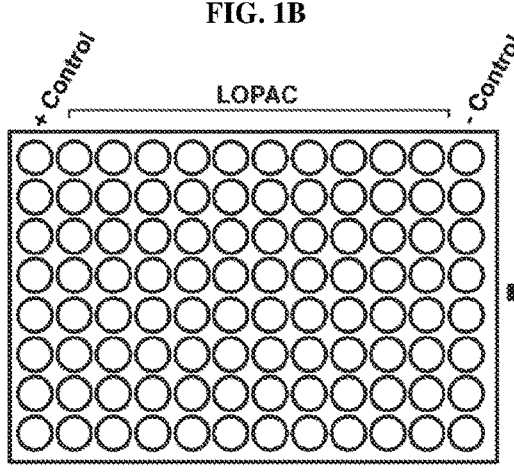
FIG. 1C
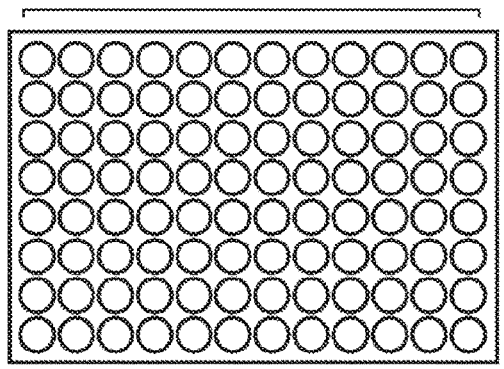
FIG. 1D
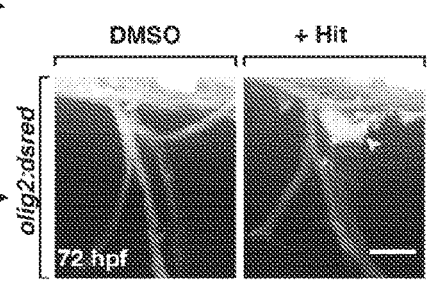
FIG. 1E

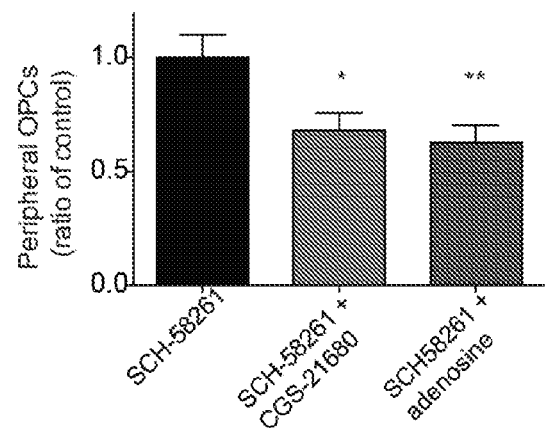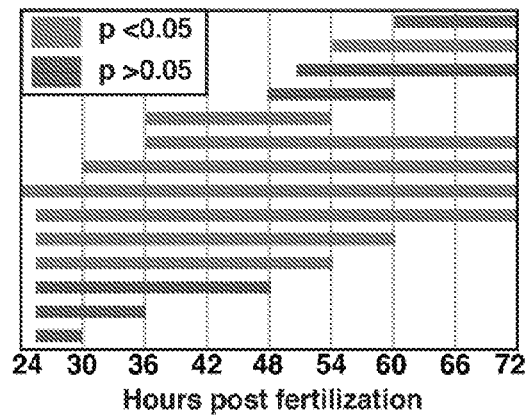
FIG. 2D                    FIG. 2E

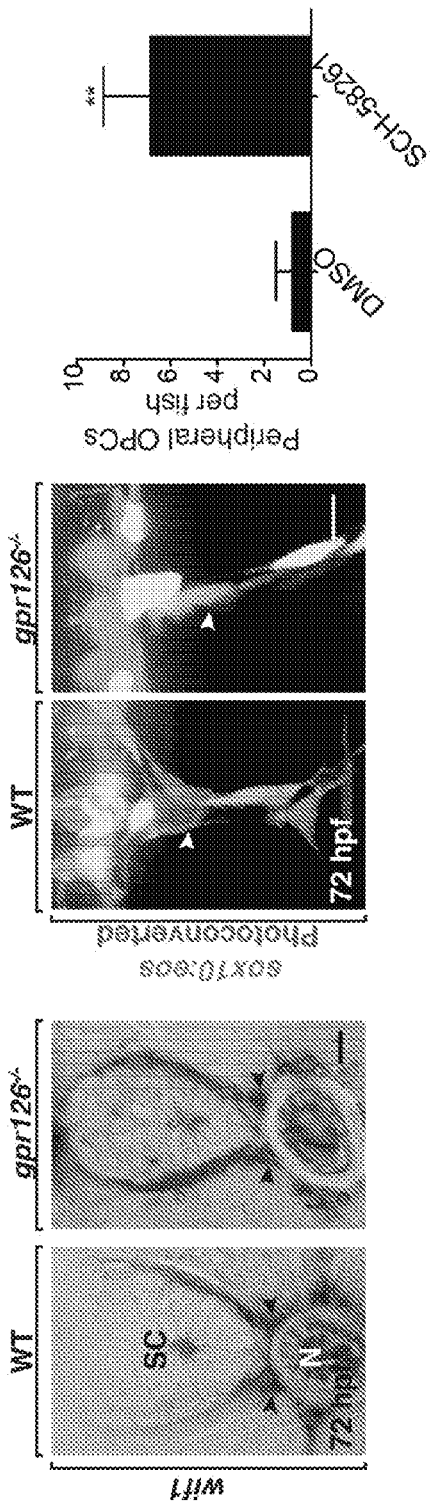
FIG. 6A
FIG. 6B
FIG. 6C
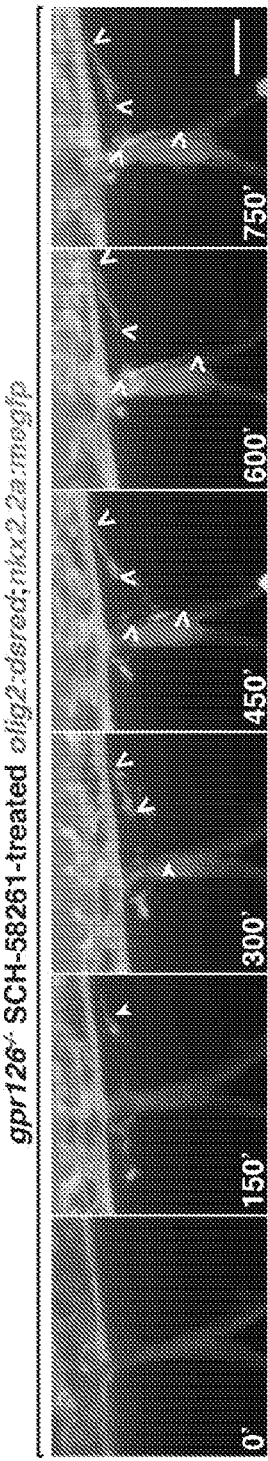
FIG. 6D

COMPOSITIONS AND METHODS FOR TREATING PERIPHERAL NERVE DISEASE, DISORDERS, AND INJURIES

CROSS REFERENCE TO RELATED APPLICATIONS

This application claims priority under 35 U.S.C. § 119(e) to U.S. Provisional Application Ser. No. 62/472,726 filed Mar. 17, 2017, the disclosure of which is incorporated by reference in its entirety herein.

STATEMENT REGARDING FEDERALLY SPONSORED RESEARCH OR DEVELOPMENT

This invention was made with government support under Grant Nos. NS072212 and NS092070, awarded by The National Institutes of Health. The government has certain rights in the invention.

BACKGROUND

Oligodendrocyte progenitor cells (OPC) are migratory, proliferative cells with multiple functions in central nervous system (CNS) development and disease (Bergles and Richardson, 2015; Emery and Lu, 2015; Zuchero and Barres, 2015), but are not known to migrate to the peripheral nervous system (PNS). These progenitors differentiate into oligodendrocytes (OL), the myelinating glia of the CNS which ensheath axons in an insulating layer of myelin that is essential for rapid propagation of action potentials (Simons and Nave, 2016). During gliogenesis, OPCs are specified from discrete precursor domains within the brain and spinal cord, but they migrate extensively to become distributed throughout the entire CNS (Miller, 2002; Rowitch, 2004). In the spinal cord, the majority of OPCs are specified from ventral pMN precursors that also give rise to motor neurons during neurogenesis (Richardson et al., 2000). These motor neurons extend axons ventrally toward the motor exit point (MEP) transition zone (TZ) and cross into the peripheral nervous system (PNS), where they ultimately innervate targets including skeletal muscle (Lewis and Eisen, 2003; Bonanomi and Pfaff, 2010). As OPCs disperse from the pMN domain to populate the spinal cord, a subset migrates ventrally toward the MEP and extends membrane processes into the TZ (Fraher and Kaar, 1984; Smith et al., 2014). However, OPC cell bodies are normally restricted from migrating through the MEP TZ and onto peripheral nerves.

The mechanisms allowing selective migration of motor axons and other glial populations, but not OPCs, through the MEP TZ are not understood. Recently, work from our lab and others showed that OPCs are capable of migrating into the PNS in zebrafish and mouse mutants with PNS defects, and peripheral OPCs have even been described in human peripheral neuropathy patients (Coulpier et al., 2010; Fröb et al., 2012; Kucenas et al., 2009; Smith et al., 2014).

Although the molecular mechanisms that mediate OPC restriction to the CNS have not yet been identified, previous work from our lab identified CNS-derived peripheral glial cells called motor exit point (MEP) glia, which are essential for preventing OPC migration onto peripheral nerves (Smith et al., 2014). A similar population known as boundary cap (BC) cells located at TZs also exists in mice and is hypothesized to regulate OPC migration at MEP TZs (Coulpier et al., 2010; Fröb et al., 2012). Specific ablation of MEP glia or BC cells without any other damage to the nerve results in OPC migration onto spinal motor nerves.

There is a long felt need in the art for compositions and methods useful for treating nervous system diseases and disorders associated with demyelination or myelination problems, particularly those of the peripheral nervous system. The present application satisfies these needs.

SUMMARY OF THE INVENTION

Disclosed herein is the unexpected result that adenosine receptor antagonists, as well as other types of compounds, stimulate peripheral OPC migration.

In order to elucidate the signals that mediate OPC segregation at motor exit point (MEP) TZs, an unbiased small molecule screen was performed. Using chemical screening and in vivo imaging, it was discovered that inhibition of A2a adenosine receptors (AR) causes ectopic OPC migration out of the spinal cord. Disclosed herein is in vivo evidence that endogenous neuromodulation by adenosine regulates OPC migration along motor axons, specifically at the MEP TZ. This work opens exciting possibilities for understanding how OPCs reach their final destinations during development and identifies mechanisms that could promote their migration in disease.

This screen identified ten small molecules that resulted in peripherally-located OPCs. It was hypothesized that adenosinergic regulation of neuronal activity at spinal motor roots may be crucial for restricting OPC migration at the MEP. It is disclosed herein that adenosine signaling through the A2a AR expressed on motor neurons functions to regulate OPC migration at MEP TZs during development, and that this regulation is dependent on neuronal activity.

The present invention therefore encompasses compositions and methods useful for stimulating oligodendrocyte progenitor cell (OPC) migration from the spinal cord onto a peripheral motor nerve by inhibiting spinal motor nerve activity. In one aspect, the inhibitor is selected from the group consisting of an inhibitor of adenosine A2a receptor (A2a AR) activity, an inhibitor of production and secretion of a neurotransmitter, an inhibitor or neuronal firing, a neurotransmitter receptor regulator, and a chloride channel blocker.

It is also disclosed herein that ablation of MEP glia promotes the migration of oligodendrocytes from the spinal cord into the PNS to myelinate axons. It is disclosed herein that adenosine signaling mediates glial-glial interactions across the motor exit point (MEP) transition zone. Without wishing to be bound by any particular theory, it is hypothesized herein that this phenomenon can be interpreted as evidence of nervous system self-repair, which if harnessed, could be used to treat childhood diseases that adversely affect peripheral nerve myelination.

The Examples below describe methods to identify and test small molecule compounds that promote the recruitment of healthy oligodendrocytes to peripheral motor axons and then evaluate target drugs in models of peripheral nerve myelination defects and associated diseases, disorders, and conditions, including injury. The invention encompasses targeted drug therapy to facilitate the migration of healthy myelinating cells from the CNS into the PNS to overcome the loss of myelin observed in diseases and disorders such as Charcot-Marie-Tooth (CMT) disease and many other peripheral myelinopathies.

Disclosed herein are methods for regulating glial-glial interaction across the CNS/PNS boundary. In one aspect, the methods are useful for regulating nerve development. In one aspect, the methods are useful for regulating nerve regeneration. In one aspect, the methods are useful for regulating the MEP TZ. In one aspect, compounds of the invention can disrupt the MEP TZ.

Disclosed herein are various types of compounds useful for recruiting OPCs. In one aspect, more than one compound can be used. In one aspect, a compound of the invention regulates migration of an OPC. The compounds of the invention can be used to recruit healthy myelinating glia into the peripheral nervous system to treat diseases where myelin is missing or damaged and to rescue myelin defects or stimulate myelination. In one aspect, a compound of the invention targets an adenosine receptor.

The present invention provides compositions and methods for regulating the A2a adenosine receptor to mediate OPC repulsion at the MEP. In one aspect, the repulsion is inhibited to allow migration to the PNS.

In one embodiment, compositions and methods are provided to stimulate OPC migration from the central nervous system to a peripheral motor nerve.

In one embodiment, the composition comprises at least one inhibitor of spinal motor nerve activity. In one aspect the composition comprises at least one A2a adenosine receptor antagonist.

In one embodiment, OPC migration is stimulated in a subject suffering from a demyelinating disease, disorder, or injury of a peripheral nerve. In one aspect, the disease, disorder, or injury is, for example, Guillain-Barre syndrome, chronic inflammatory demyelinating polyneuropathy (CIDP), anti-MAG peripheral neuropathy, Charcot-Marie-Tooth disease, Hereditary neuropathy with liability to pressure palsy, a copper deficiency associated condition, or progressive inflammatory neuropathy.

Copper deficiencies are associated with peripheral neuropathy, myelopathy, and rarely optic neuropathy.

In one embodiment, to induce OPC migration or treat a disease, disorder, or injury with myelination or demyelination issues in the PNS, a pharmaceutical composition comprising a therapeutically effective amount of at least one compound of the invention is administered to a subject. In one aspect, the pharmaceutical compositions comprises at least two compounds of the invention. In one aspect, the pharmaceutical composition comprises a pharmaceutically acceptable carrier. In one aspect, the pharmaceutical composition comprises at least one additional therapeutic agent.

It is disclosed herein that the non-selective adenosine receptor antagonist CGS-15943 stimulates peripheral OPC migration, that is, it unexpectedly induces ectopic migration from the CNS to peripheral motor neurons.

It is disclosed herein that the selective A2a adenosine receptor antagonist SCH-58261 unexpectedly stimulates an increase in peripheral olig2+ cells.

Some A2a AR antagonists useful for stimulating OPC migration to the PNS include, but are not limited to: CGS-15943, SCH-58261, istradefylline (KW-6002), preladenant (SCH-420,814), ATL-444, MSX-3, SCH-412,348, SCH-442,416, ST-1535, caffeine, VER-6623, VER-6947, VER-7835, vipadenant (BIIB-014), ZM-241,385, and theophylline. In one embodiment, a subject in need thereof is administered a therapeutically effective amount one or more of these compounds or a compound with similar activity. In one aspect, a single treatment with one or more compounds of the invention stimulates OPC migration to the PNS and myelination on peripheral motor nerves once OPC migration has occurred. In one aspect, a second treatment is administered. In one aspect, a second treatment is administered once OPC migration has started. In another aspect, a second treatment is administered after migration has occurred. In one aspect, three or more treatments are administered.

Other types of compounds are also disclosed herein to stimulate OPC migration. Compounds disclosed herein include an inhibitor of production and secretion of a neurotransmitter, an inhibitor or neuronal firing, a neurotransmitter receptor regulator, and a chloride channel blocker. In one aspect, inhibitor of production and secretion of a neurotransmitter is 1-phenyl-3-(2-thiazolyl)-2-thiourea or brefeldin A. In another aspect, the inhibitor of neuronal firing is tetanus toxin light chain (TeNT) or carbenoxolone. In one aspect, the neurotransmitter receptor regulator is an agonist of a neurotransmitter receptor and is selected from the group consisting of acetylthiocholine chloride or salmeterol xinafoate. In another aspect, the chloride channel blocker is N-phenylanthranilic acid. Other useful compounds include I-OMe-tyrphostin AG 538, L-canavanine sulfate, clofibrate, and wortmannin.

It is also disclosed herein that regulators of the $\alpha$-amino-3-hydroxy-5-methyl-4-isoxazolepropionic acid receptor (AMPAR) and the N-methyl-D-aspartate receptor (NMDAR) are useful for stimulating OPC migration. For example, a useful AMPAR antagonist is 2,3-Dioxo-6-nitro-1,2,3,4-tetrahydrobenzo[f]quinoxaline-7-sulfonamide (NBQX) and a useful NMDAR antagonist is (5S,10R)-(+)-5-Methyl-10,11-dihydro-5H-dibenzo[a,d]cyclohepten-5,10-imine maleate (MK-801).

It is disclosed herein that OPCs and MEP glia share a common precursor.

It is disclosed herein that A2a adenosine receptor antagonists do not disrupt normal glia development.

It is disclosed herein that A2a adenosine receptors are required to regulate OPC migration.

In one aspect, a compound of the invention is administered intravenously. In one aspect, it can be introduced into the cerebrospinal fluid. In one aspect, it can be introduced intrathecally. In one aspect, it can be administered epidurally. In one aspect, it can be administered as a liquid. In one aspect, it can be administered intracisternally. One of ordinary skill in the art will appreciate that various routes of administration can be used and that doses may vary depending on factors such as the age, weight, sex, and health of the subject.

In one embodiment, a dose of a compound of the invention can range from about 0.1 µg/kg to about 100 mg/kg body weight. In one aspect, it can range from about 1.0 µg/kg to about 50 mg/kg. In another aspect, it can range from about 5.0 µg/kg to about 75 mg/kg. In yet another aspect, a dose can range from about 5.0 µg/kg to about 25 mg/kg. In another aspect, the dose ranges from about 0.001 mg/kg body weight to about 100 mg/kg body weight. In one aspect, the dose ranges from about 0.01 mg/kg body weight to about 10 mg/kg body weight. For example, a dose could be about 0.001, 0.01, 0.1, 0.2, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35, 40, 45, 50, 60, 70, 80, 90, or about 100 mg/kg body weight.

In one aspect, a unit dose of a compound of the invention can be administered. Depending on the dose given to a subject, it can also be administered more than once and when administered more than once the intervals can be varied and the dose and intervals can be determined by the physician. For example, compound can be administered as a unit dose ranging from about 0.1 mg to about 100 mg. In one aspect, it can be administered as a unit dose ranging from about 1.0 mg to about 10 mg. Unit doses include, but are not limited to, about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 24.5, 25.0, 25.5, 26.0, 26.5, 27.0, 27.5, 28.0, 28.5, 29.0, 29.5, 30, 35, 40, 45, 50, 55, 60, 65, 70, 75, 80, 85, 90, 95, and 100 mg per dose, and all numbers and fractions subsumed within that range.

In one aspect, a compound of the invention can be administered with another type of drug or agent, such a different type of inducer of OPC migration or with a therapeutic compound or antibiotic, or with a combination thereof.

In one embodiment, one or more compounds of Table 1 is administered to a subject in need thereof to induce OPC migration from the central nervous system.

Various aspects and embodiments of the invention are described in further detail below.

BRIEF DESCRIPTION OF THE DRAWINGS

FIG. 1 comprises FIGS. 1A-1E. A small molecule screen identifies compounds that disrupt OPC migration at the MEP TZ. (A) Schematic of a transverse view of the MEP TZ. MEP glia prevent OPC exit from the spinal cord. OPC processes (yellow, arrow) contact MEP glia (green) but are repelled. Without MEP glia, OPCs migrate onto peripheral nerves. (B) Schematic showing setup of primary screen. One or two embryos per well were treated with a single compound from the LOPAC library. AG1478 was the positive (+) control and 1% DMSO was the negative (−) control for each plate. (C) Low magnification images showing lateral views of negative (top) and positive (bottom) controls at 72 hpf. (D) Positive hits were repeated in triplicate and randomized with positive and negative controls in a blind secondary screen. (E) Images of 72 hpf olig2:dsred larvae control and validated hits showing ectopic OPC (arrowhead) on the peripheral nerve. Scale bar, (C) 100 µM (E) 20 µM.

gpr126$^{-/-}$ larva treated with SCH-58261 from 36 to 72 hpf 0' is 57 hpf. Arrowheads mark a nkx2.2$^+$olig2$^+$ OPC ensheathing motor axons. (E) Images of MBP antibody (arrowheads) on peripheral nerves of 4 dpf olig2:dsred; gpr126$^{-/-}$ larvae treated with DMSO or SCH-58261 from 36 to 72 hpf. Asterisk marks peripheral OPC. (F) Live images of olig2:dsred;mbp:egfp-CAAX larvae treated with DMSO or SCH-58261 from 36 to 72 hpf Asterisk marks olig2$^+$ peripheral OPC with mbp$^+$ membrane sheaths (arrowheads) around peripheral motor axons Scale bars, 20 μm.

Figure 7:
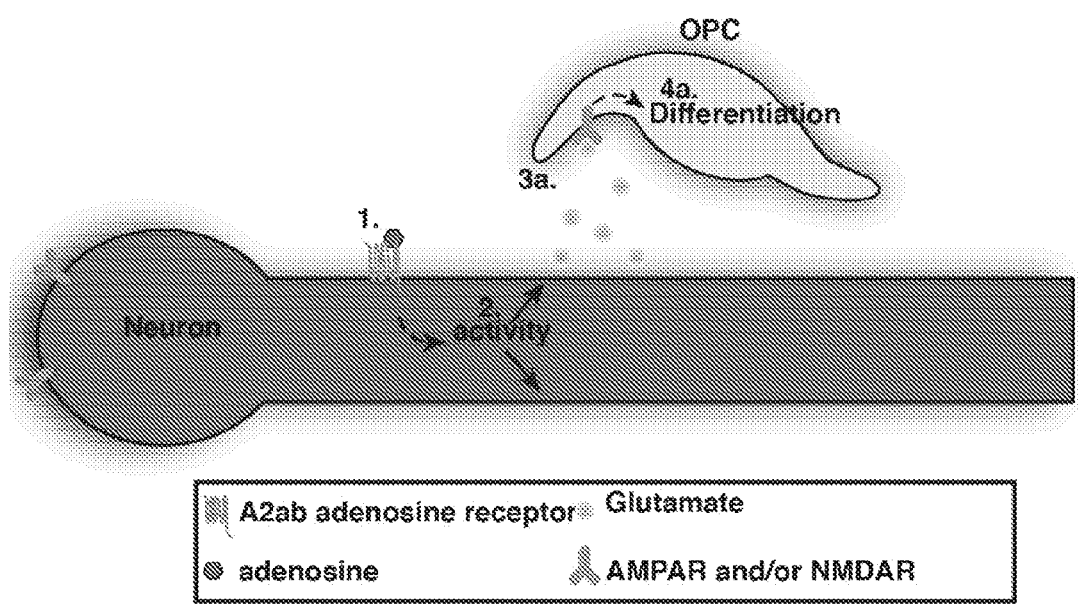

FIG. 7. Schematic Model of OPC migration regulated by A2a AR neuromodulation. 1. Adenosine binds to A2ab AR on neurons, modulating neuronal activity. 2. Increased activity causes increased release of glutamate at axo-glial synapses, or via non-synaptic release into the extracellular space. 3. Neurotransmitters or other factors bind to receptors on OPCs. 4. Activation of the receptor(s) promotes OPC differentiation and decreased migration.

FIG. 8 comprises FIGS. 8A-8G. A2a AR specifically mediates OPC migration at the MEP TZ. (A-C) Dose responses for antagonists selective for A1 (CPT), A2b (MRS 1754), and A3 (MRS 1191). (D) Mean±SEM dorsal olig2$^+$ cells at 72 hpf in olig2:dsred larvae treated with DMSO (n=11), CGS-21680 (n=9), or adenosine (n=4), p=0.23. (E-G) Numbers of peripheral OPCs in larvae treated with 10 μM SCH-58261 during various developmental stages. All data presented are mean±SEM. * p<0.05,  p<0.01, * p<0.001 compared to DMSO, n=9-12 fish per condition.

Figure 9:
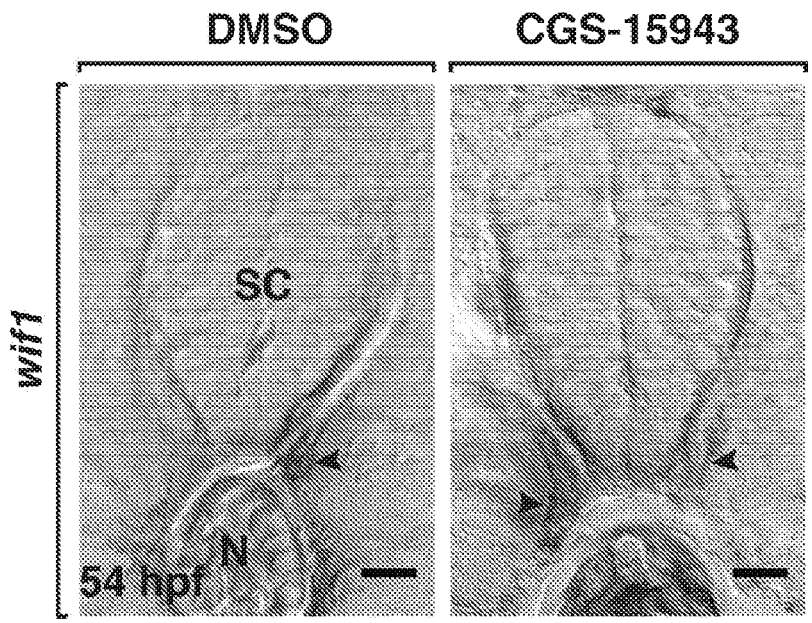

FIG. 9, comprises left and right panels. Drug treated larvae have wif1$^+$ MEP glia. In situ hybridization for wif1 in 54 hpf larvae treated 36 to 72 hpf with DMSO (left panel) or 1.25 μM CGS-15943 (right panel). Arrowheads mark MEP glia. SC, spinal cord; N, notochord. Scale bar, 20 μm.

FIG. 10 comprises FIGS. 10A-10F. Characterization of adora2aa mutant larvae. (10A) Survival of adora2aa$^{-/-}$ larvae compared to WT. p=0.30, n=50 fish. (10B) Percent of fish successfully hatched out of the chorion by 2 and 3 dpf. p=0.18, n=50 fish. (10C) Percentage of larvae with positive (+) and negative (−) startle responses at 3 dpf p=0.38, n=25 (A2aa$^{-/-}$) n=34 (WT). (10D) Heart rate in WT and A2aa mutant larvae at 50 hpf. p=0.18, n=20 (A2aa$^{-/-}$) n=21 (WT). (10E) Brightfield images of 3 dpf WT and adora2aa$^{-/-}$ larvae. (10F) Mean SEM of peripheral OPCs per larvae for heterozygous adora2aa$^{+/-}$ and homozygous adora2aa$^{-/-}$ larvae at 3 dpf. p=0.24, n=20 (adora2aa$^{+/-}$) n=26 (adora2aa$^{-/-}$). Scale bar, 0.5 mm.

Figure 11A:
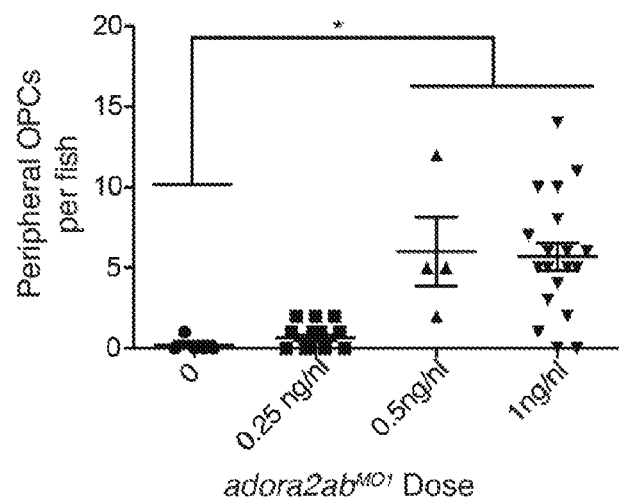
Figure 11B:
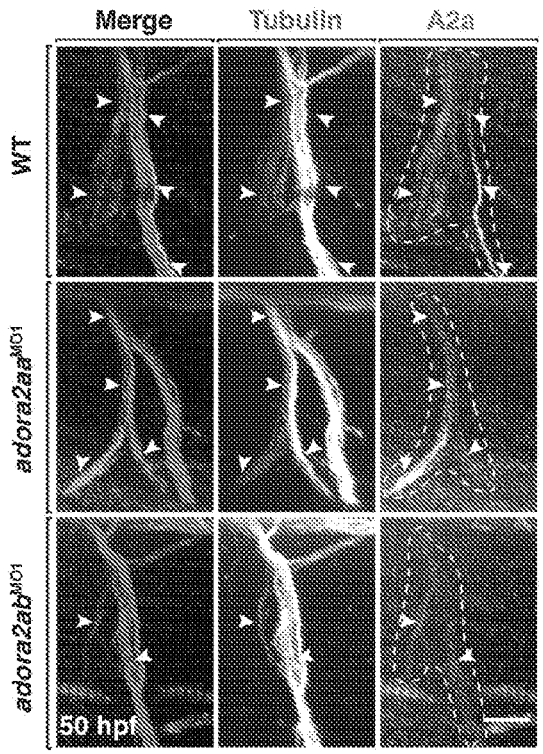
Figure 11C:
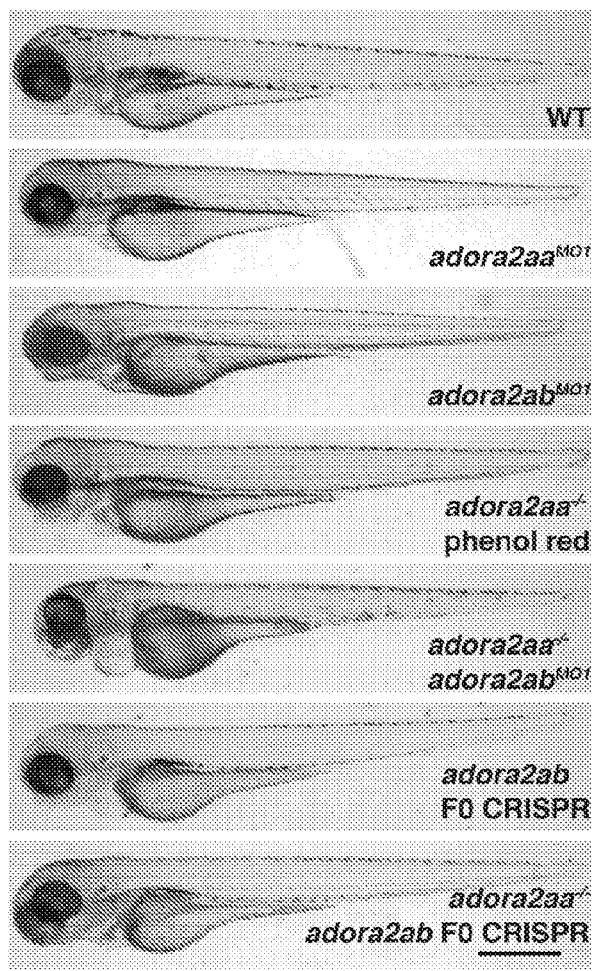

FIG. 11 comprises FIGS. 11A-11C. Validation of adora2ab MOs. (A) Dose response for adora2ab$^{MOI}$. Data are mean±SEM peripheral OPCs per larva at 3 dpf. n=4 to 19 larvae per dose, * p<0.01. (B) Images of peripheral nerves in WT larvae or larvae injected with adora2aa$^{MOI}$ or adora2ab$^{MOI}$ labeled with A2a antibody. Arrowheads mark motor and sensory axons. Yellow outlines show example ROIs used for quantification. (C) Brightfield images of 3 dpf WT or adora2aa$^{-/-}$ injected with MO or sgRNA. Scale bars, (B) 20 μM, (F) 0.5 mm.

Figure 12:
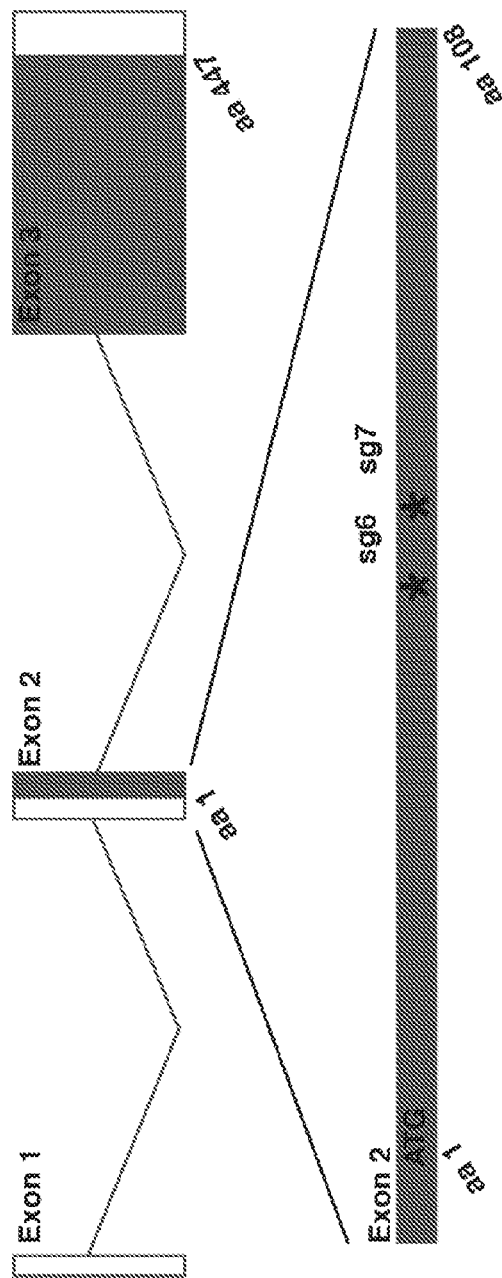

FIG. 12. Adora2ab CRISPR-induced indels. Schematic representation of adora2ab gene and regions targeted by sgRNA 6 and sgRNA 7.

Figure 13A:
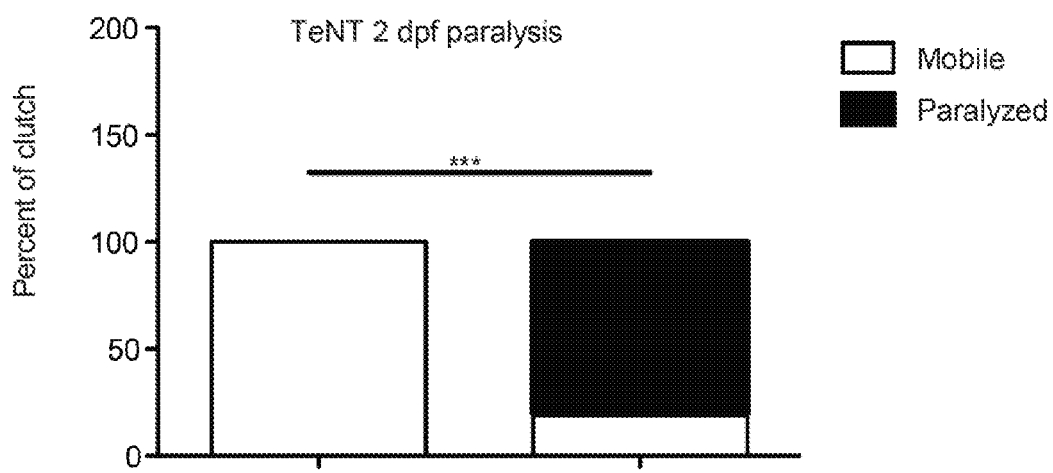
Figure 13B:
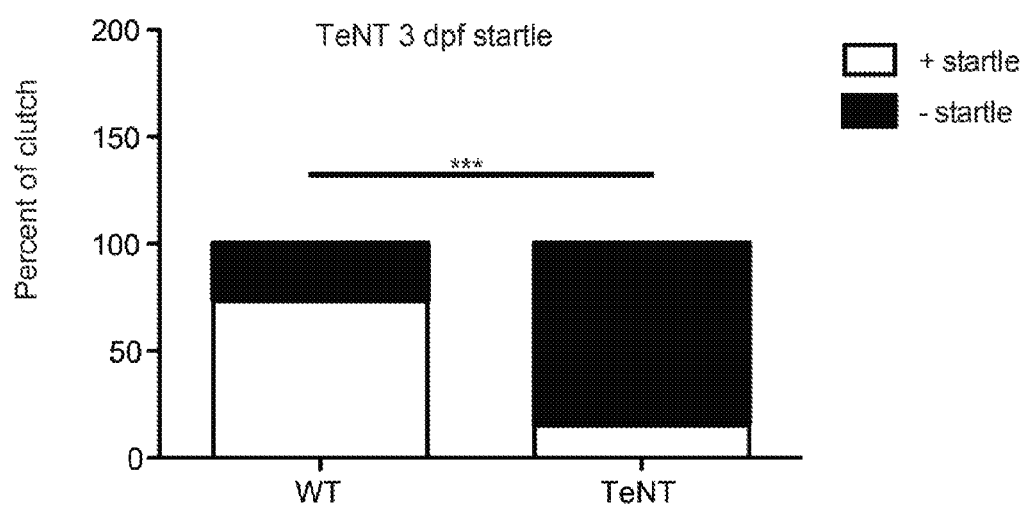

FIG. 13 comprises FIGS. 13A-13B. TeNT mRNA paralyzes larvae. (A) Percentage of embryos that moved or didn't move during dechorionation with forceps at 2 dpf Analyzed by Chi-squared test; p<0.0001, n=54 (WT), n=57 (TeNT). (B) Percentage of fish with positive and negative startle responses at 3 dpf. Analyzed by Fisher's exact test; p<0.0001, n=52 (WT), n=53 (TeNT). Scale bar, 20 μM.

DETAILED DESCRIPTION

Abbreviations and Acronyms

AR—adenosine receptor
A2a AR—A2a adenosine receptor; also known as ADORA2A
AMPA—α-amino-3-hydroxy-5-methyl-4-isoxazolepropionic acid
AMPAR—AMPA receptor
BC—boundary cap
BCC—boundary cap cells
CIDP—chronic inflammatory demyelinating polyneuropathy
CMT—Charcot-Marie-Tooth Disease
CNS—central nervous system
CRISPR—Clustered Regularly Interspaced Short Palindromic Repeat
DRG—dorsal root ganglion
GPCR—G protein-coupled receptor
hpf—hour-post-fertilization
LOPAC1280—library of pharmacologically active compounds
HotSHOT—hot sodium hydroxide and tris
MBP—myelin basic protein
MEP—motor exit point
MK-801—Dizocilpine; (5S,10R)-(+)-5-Methyl-10,11-dihydro-5H-dibenzo[a,d]cyclohepten-5,10-imine maleate
mn—motor neuron
MO—morpholino oligonucleotide
N—notochord
NBQX—2,3-Dioxo-6-nitro-1,2,3,4-tetrahydrobenzofquinoxaline-7-sulfonamide
nc—neural crest
NMDA—N-methyl-D-aspartate
NMDAR—NMDA receptor
OL—oligodendrocyte
OPC—oligodendrocyte progenitor cell
pg—perineurial glia precursors (also referred to as PG)
PNS—peripheral nervous system
SC—spinal cord
SCs—Schwann cells
TALEN—transcription activator-like effector nucleases
TeNT—tetanus toxin light chain
TZ—transition zone
wif1—wnt inhibitory factor 1
WT—wild type
ZIRC—Zebrafish International Resource Center Definitions In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

The term "adult" as used herein, is meant to refer to any non-embryonic or non-juvenile subject. For example the term "adult adipose tissue stem cell," refers to an adipose stem cell, other than that obtained from an embryo or juvenile subject.

As used herein, an "agonist" is a composition of matter which, when administered to a mammal such as a human, enhances or extends a biological activity attributable to the level or presence of a target compound or molecule of interest in the mammal.

A disease or disorder is "alleviated" if the severity of a symptom of the disease, condition, or disorder, or the frequency with which such a symptom is experienced by a subject, or both, are reduced.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

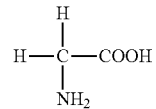

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "analgesia", as used herein, refers to absence of sensibility to pain, particularly the relief of pain without loss of consciousness; absence of pain or noxious stimulation.

As used herein, an "analog", or "analogue" of a chemical compound is a compound that, by way of example, resembles another in structure but is not necessarily an isomer (e.g., 5-fluorouracil is an analog of thymine).

As used herein, "anesthesia" refers to loss of the ability to feel pain and a partial or complete loss of sensation, caused by administration of a drug or other medical intervention and is a local or general insensibility to pain with or without the loss of consciousness. "Epidural anesthesia" refers to that produced by injection of the anesthetic into the extradural space, either between the vertebral spines or into the sacral hiatus (caudal block). "General anesthesia" refers to a state of unconsciousness and insusceptibility to pain, produced by administration of anesthetic agents by, for example, inhalation, intravenously, intramuscularly, rectally, or via the gastrointestinal tract. "Spinal anesthesia" refers to a regional anesthesia by injection of a local anesthetic into the subarachnoid space around the spinal cord.

The term "anesthetic", as used herein, refers to a drug or agent capable of producing a complete or partial loss of feeling (anesthesia).

An "antagonist" is a composition of matter which when administered to a mammal such as a human, inhibits a biological activity attributable to the level or presence of a compound or molecule of interest in the mammal.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound," as used herein, refers to any type of substance or agent that is commonly considered a drug, or a candidate for use as a drug or biologic, as well as combinations and mixtures of the above.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject.

The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "ingredient" refers to any compound, whether of chemical or biological origin, that can be used in cell culture media to maintain or promote the proliferation, survival, or differentiation of cells. The terms "component", "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibitor" as used herein, refers to any compound or agent, the application of which results in the inhibition of a process or function of interest, including, but not limited to, differentiation and activity. Inhibition can be inferred if there is a reduction in the activity or function of interest.

By "inhibitor of adenosine A2a receptor (A2a AR) activity" is meant an agent that blocks the expression, levels, or activity of the A2a AR.

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

Used interchangeably herein are the terms "isolate" and "select".

The term "isolated," when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays which distinguish cell types.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "modulate", as used herein, refers to changing the level of an activity, function, or process. The term "modulate" encompasses both inhibiting and stimulating an activity, function, or process.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

"Pharmaceutically acceptable" means physiologically tolerable, for either human or veterinary application.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, "pharmaceutical compositions" include formulations for animal use, including human and veterinary use.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder.

A prophylactic or preventative treatment is administered for the purpose of decreasing the risk of developing pathology associated with developing the disease or disorder.

A "prophylactic" treatment is a treatment administered to a subject who does not exhibit signs of a disease or exhibits only early signs of the disease for the purpose of decreasing the risk of developing pathology associated with the disease.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest. Regulate is used interchangeably with modulate.

A "reversibly implantable" device is one which may be inserted (e.g. surgically or by insertion into a natural orifice of the animal) into the body of an animal and thereafter removed without great harm to the health of the animal.

As used herein, the term "secondary antibody" refers to an antibody that binds to the constant region of another antibody (the primary antibody).

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%. The term "stimulator" as used herein, refers to any compound or agent, the application of which results in the stimulation of a process or function of interest, including, but not limited to, ASC cell production, differentiation, and activity, as well as that of ASC progeny.

A "subject" of analysis, diagnosis, or treatment is an animal. Such animals includes pets, livestock, veterinary animals, birds, and fish. Such animals also include mammals, preferably a human.

As used herein, a "subject in need thereof" is a patient, animal, mammal, or human, who will benefit from the method of this invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents.

For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl@ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure.

The heteroaryl rings described herein may be substituted on carbon or on a nitrogen atom if the resulting compound is stable.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

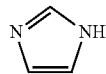

is understood to represent a mixture of the structures:

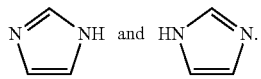

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

EMBODIMENTS

The present application discloses the unexpected result that OPCs can be stimulated to leave the CNS and migrate out to peripheral motor nerves. In one embodiment, migration can be stimulated using an antagonist of the adenosine A2a receptor.

In one embodiment, the compositions and methods of the invention are useful for treating demyelinating diseases, disorders, and conditions.

In one embodiment, the compositions and methods are useful for stimulating oligodendrocyte progenitor cell (OPC) migration from the spinal cord onto a peripheral motor nerve in a subject. In one embodiment, migration can be stimulated using an antagonist of the adenosine A2a receptor. In one aspect, the method is useful for treating demyelination diseases and disorders in the periphery because once the OPCs have migrated they start making myelin at the site of demyelination.

It is disclosed herein that adenosine signaling mediates glial-glial interactions across the motor exit point (MEP) transition zone. The present application further discloses the unexpected result that adenosine receptor antagonists stimulate peripheral OPC migration. It is disclosed herein that ablation of MEP glia promotes the migration of oligodendrocytes from the spinal cord into the PNS to myelinate axons.

Extracellular adenosine can signal through a set of four purinergic G-protein-coupled receptors: A1, A2a, A2b, and A3, that is, adenosine is an endogenous ligand of the receptors. Adenosine initiates its biological effects via these four receptor subtypes. The A1 and A2a AR possess high affinity for adenosine while the A2b and A3 AR show relatively lower affinity for adenosine receptors. The adenosine A2a receptor is also known as ADORA2A and A2a AR. This protein is a member of the G protein-coupled receptor (GPCR) family which possess seven transmembrane alpha helices.

The compounds of the invention can be used to recruit healthy myelinating glia into the peripheral nervous system to treat diseases where this myelin is missing or damaged and to rescue myelin defects or stimulate myelination. In one aspect, a compound of the invention targets an adenosine receptor. In one aspect, a receptor identified or a pathway identified herein are targeted by a compound of the invention.

The present invention provides compositions and methods for regulating the A2a adenosine receptor to mediate OPC repulsion at the MEP.

The Examples describe methods to identify small molecule compounds that promote the recruitment of healthy oligodendrocytes to peripheral motor axons and then evaluate target drugs in models of peripheral nerve myelination defects and associated diseases, disorders, and conditions. In one aspect, the disease, disorder, or condition is CMT.

In another embodiment, the present application provides compositions and methods for inhibiting OPC migration.

Disclosed herein are methods for regulating glial-glial interaction across the CNS/PNS boundary. In one aspect, the methods are useful for regulating nerve development. In one aspect, the methods are useful for regulating nerve regeneration. In one aspect, the methods are useful for regulating the MEP TZ. In one aspect, compounds of the invention can disrupt the MEP TZ.

It is disclosed herein that the non-selective adenosine receptor antagonist CGS-15943 stimulates ectopic peripheral OPC migration.

It is disclosed herein that the selective A2a antagonist SCH-58261 stimulates an increase in peripheral olig2+ cells.

It is disclosed herein that A2a antagonists do not disrupt normal glia development.

The A2a AR antagonist istradefylline (KW-6002) has been used in multiple clinical trials for such things as advanced Parkinson's Disease, and has been used at various dosages, including 2, 5, 10, 20, 40, 60, and 80 mg/day for time periods of up to 1 year (see, for example, 6002-US-001, NCT00456856, NCT00456794, NCT00199407, NCT000955054, NCT00455507, NCT00955526, NCT00199420). CGS 15943, SCH 58261, and ZM 241385 has been used in various mammals for things such as effects on locomotor activity, discriminative effects, cerebral ischemia, etc. Doses have ranged from 0.1 to 10 mg/kg and included 0.01, 0.1, 0.2, 1.0, 2.0 and 10 mg/kg body weight. Routes of administration have included, for example, intraperitoneal, intramuscular, and intravenous.

Clinical trials using SCH 420184 in treating Parkinson's have included doses of 2, 5, and 10 mg orally.

In one embodiment, the compositions and methods of the invention are useful for treating diseases and disorders including, but not limited to, Guillain-Barre syndrome and its chronic counterpart, chronic inflammatory demyelinating polyneuropathy (CIDP), anti-MAG peripheral neuropathy, Charcot-Marie-Tooth disease and its counterpart Hereditary neuropathy with liability to pressure palsy, copper deficiency associated conditions (peripheral neuropathy, myelopathy, and rarely optic neuropathy), and progressive inflammatory neuropathy.

In one embodiment, a compound of the invention induces OPC migration from the central nervous system to the peripheral nervous system. In one aspect, once the OPC have migrated to the peripheral nervous they myelinate the nerves onto which they migrated. Others who have used similar drugs have only studied the effects in the central nervous system on CNS diseases such as multiple sclerosis (MS) and Parkinson's disease, not the peripheral nervous system.

Some useful A2a AR antagonists include, but are not limited to: CGS-15943, SCH-58261, istradefylline (KW-6002), preladenant (SCH-420,814), ATL-444, MSX-3, SCH-412,348, SCH-442,416, ST-1535, caffeine, VER-6623, VER-6947, VER-7835, vipadenant (BIIB-014), ZM-241,385, and theophylline.

Structures and chemical names for some A2a AR antagonist compounds of the invention are:
CGS-15943—(9-Chloro-2-(2-furanyl)-[1,2,4]triazolo[1,5-c]quinazolin-5-amine); CAS Number 104615-18-1

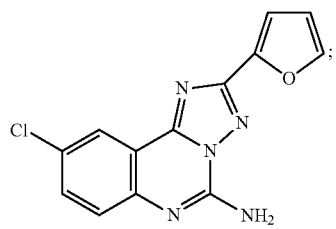 [SMILES: Nc1nc2ccc(Cl)cc2c2nc(-c3ccco3)nn12]

SCH-58261 (also referred to as SCH 58261; 7-(2-phenyl-ethyl)-5-amino-2-(2-furyl)-pyrazolo-[4,3-e]-1,2,4-triazolo [1,5-c]pyrimidine); CAS Number 160098-96-4

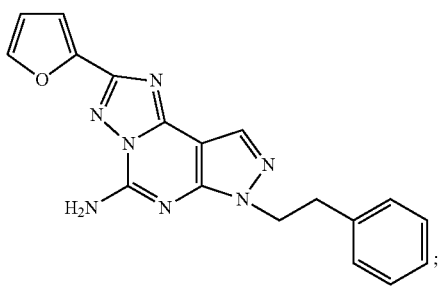 [SMILES: Nc1nc2c(cnn2CCc2ccccc2)c2nc(-c3ccco3)nn12]

KW-6002 (also referred to as istradefylline; 8-[(1E)-2-(2-(3,4-Dimethoxyphenyl)ethenyl]-1,3-diethyl-3,7-dihydro-7-methyl-1H-purine-2,6-dione), CAS Number 155270-99-8

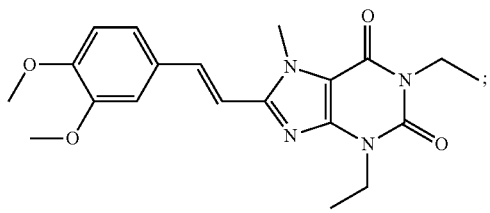 [SMILES: CCn1c(=O)c2c(nc(/C=C/c3ccc(OC)c(OC)c3)n2C)n(CC)c1=O]

and
SCH-420,814 (also referred to as preladenant; 2-(furan-2-yl)-7-(2-(4-(4-(2-methoxyethoxy)phenyl)piperazin-1-yl) ethyl)-7H-pyrazolo[4,3-e][1,2,4]triazolo[1,5-c]pyrimidin-5-amine); CAS Number 377727-87-2

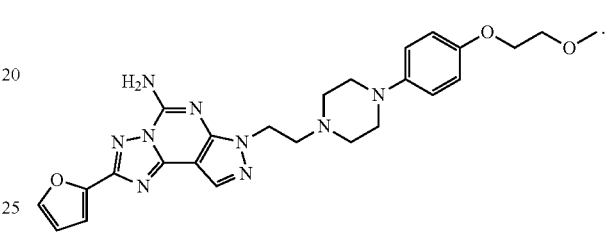

Chemical names for some of the compounds of the invention include:
ATL-444—(1S,3R)-1-{[6-Amino-9-(2-propyn-1-yl)-9H-purin-2-yl]ethynyl}-3-methylcyclohexanol; Pubchem ID 11616539
MSX-3—((E)-phosphoric acid mono-[3-[8-[2-(3-methoxyphenyl)vinyl]-7-methyl-2,6-dioxo-1-prop-2-ynyl-1,2,6,7-tetrahydropurin-3-yl] propyl] ester disodium salt)
SCH-412,348—7-{2-[4-(2,4-difluoro-phenyl)-piperazin-1-yl]-ethyl}-2-furan-2-yl-7H-pyrazolo[4,3-e][1,2,4]triazolo [1,5-c]pyrimidin-5-ylamine; PubChem CID: 9912318
SCH-442,416—2-(2-Furanyl)-7-[3-(4-methoxyphenyl) propyl]-7H-pyrazolo [4,3-e][1,2,4]triazolo[1,5-c]pyrimidin-5-amine; CAS Number 316173-57-6
ST-1535-2-butyl-9-methyl-8-(triazol-2-yl)purin-6-amine; CAS Number 496955-42-1
VER-6623-2-isopropyl-4-(thiazol-2-yl)thieno[3,2-d]pyrimidine
ZM-241,385—4-(2-[7-amino-2-(2-furyl)[1,2,4]triazolo [2,3-a][1,3,5]triazin-5-ylamino]ethyl)phenol
AMPA receptor—The α-amino-3-hydroxy-5-methyl-4-isoxazolepropionic acid receptor (also known as AMPA receptor, AMPAR, or quisqualate receptor) is an ionotropic transmembrane receptor for glutamate that mediates fast synaptic transmission in the central nervous system (CNS). It has been traditionally classified as a non-NMDA-type receptor, along with the kainate receptor. Its name is derived from its ability to be activated by the artificial glutamate analog AMPA. The receptor was first named the "quisqualate receptor" by Watkins and colleagues after a naturally occurring agonist quisqualate and was only later given the label "AMPA receptor" after the selective agonist developed by Tage Honore and colleagues at the Royal Danish School of Pharmacy in Copenhagen. AMPARs are found in many parts of the brain and are the most commonly found receptor in the nervous system.

Regarding the signaling pathway involved, it is disclosed herein that the AMPAR antagonist NBQX (2,3-Dioxo-6-nitro-1,2,3,4-tetrahydrobenzoquinoxaline-7-sulfonamide) can stimulate OPC migration to the periphery, as can the NMDAR antagonist MK-801 (Dizocilpine; (5S,10R)-(+)-5-Methyl-10,11-dihydro-5H-dibenzo[a,d]cyclohepten-5,10-imine maleate; CAS No.: 77086-22-7) (see FIG. 5, particularly 5G and 5H).

NMDA receptor—The N-methyl-D-aspartate receptor (also known as the NMDA receptor or NMDAR), is a glutamate receptor and ion channel protein found in nerve cells. The NMDA receptor is one of three types of ionotropic glutamate receptors, the others being the AMPA and kainate receptors. It is activated when glutamate and glycine (or D-serine) bind to it, and when activated it allows positively charged ions to flow through the cell membrane. The NMDA receptor is very important for controlling synaptic plasticity and memory function.

The NMDAR is a specific type of ionotropic glutamate receptor. The NMDA receptor is so named because the agonist molecule N-methyl-D-aspartate (NMDA) binds selectively to it, and not to other glutamate receptors. Activation of NMDA receptors results in the opening of an ion channel that is nonselective to cations, with a combined reversal potential near 0 mV. While the opening and closing of the ion channel is primarily gated by ligand binding, the current flow through the ion channel is voltage dependent. Extracellular magnesium ($Mg^{2+}$) and zinc ($Zn^{2+}$) ions can bind to specific sites on the receptor, blocking the passage of other cations through the open ion channel. Depolarization of the cell dislodges and repels the $Mg^{2+}$ and $Zn^{2+}$ ions from the pore, thus allowing a voltage-dependent flow of sodium ($Na^+$) and small amounts of calcium ($Ca^{2+}$) ions into the cell and potassium ($K^+$) out of the cell.

According to an embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European or foreign counterpart).

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into the composition of the present invention include, but are not limited to, bone growth factors (e.g., BMP, OP-1), basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-.alpha. and TGF-.beta.), interleukin-8 (IL-8), granulocyte-macrophage colony stimulating factor (GM-CSF), the interleukins, and the interferons.

Other agents or compounds that can be incorporated into the composition of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

In one embodiment, the biologically active agents or compounds can first be encapsulated into microcapsules, microspheres, microparticles, microfibers, reinforcing fibers and the like to facilitate mixing and achieving controlled, extended, delayed and/or sustained release and combined with the cells of the invention. Encapsulating the biologically active agent can also protect the agent against degradation during formation of the composite of the invention.

In an embodiment of the invention, the biologically active agent is controllably released into a subject.

As described herein, the compositions of the present invention comprise, as an active agent, at least one compound having the structure of, or is an analog or derivative of any of the formulas or compounds disclosed herein. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

In cases where compounds are sufficiently basic or acidic to form acid or base salts, use of the compounds as salts may be appropriate. Examples of acceptable salts are organic acid addition salts formed with acids that form a physiologically acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the health, sex, and age of the subject, etc.

In some embodiments, the methods of the present invention comprise co-administering a neurotransmitter receptor modulating agent and an immunomodulatory agent. Co-administered agents can be administered together or separately, simultaneously or at different times. When administered, the neurotransmitter receptor modulating agent and the immunomodulatory agent independently can be administered once, twice, three, four times daily or more or less often, as needed. In some embodiments, the agents are administered once daily. In some embodiments, the agents are administered at the same time or times, for instance as an admixture. One or more of the agents can be administered in a sustained-release formulation.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. The two active agents can both be simulators of OPC migration. In some embodiments, co-administration can be accomplished by co-formulation, i.e., preparing a single pharmaceutical composition including both active agents (i.e., the neurotransmitter receptor modulating agent and the immunomodulatory agent are administered as a single formulation). In other embodiments, the active agents can be formulated separately (i.e., the neurotransmitter receptor modulating agent and the immunomodulatory agent are administered as separate formulations). In another embodiment, the active and/or adjunctive agents may be linked or conjugated to one another.

Pharmaceutical compositions that are useful in the methods of the invention may be administered systemically in oral solid formulations, ophthalmic, suppository, aerosol, injectable, topical or other similar formulations.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

The composition may be formulated with a "mucosal penetration enhancer," i.e., a reagent that increases the rate or facility of transmucosal penetration, such as, but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

In one embodiment, administration is oral. In one aspect, administration is once per day. In one aspect, administration is twice per day. In one aspect, administration is once per week. In one aspect, administration is twice per week. One of ordinary skill in the art can appreciate that for the treatments described herein the amount and frequency can be varied for various reasons, including the age, weight, health and sex of the individual.

Generally, the concentration of a compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 µg to about 100 mg/kg body weight of the recipient, from about 10 µg to about 75 mg/kg, about 3 µg to about 50 mg/kg, about 6 µg to 90 mg/kg, and about 15 µg to 60 mg/kg. In one aspect, a dose is about 0.001, 0.01, 1, 2, 3, 4, 5, 6, 7, 8, 9, 10, 11, 12, 13, 14, 15, 16 17, 18, 19, 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 540, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg. Administration can be per day, per treatment, or per procedure. In one aspect, more than one dose can be administered or a dose can be broken up into smaller sub-unit doses.

A compound can be conveniently administered in unit dosage form; for example, containing 5 to 1000 mg, conveniently 10 to 750 mg, most conveniently, 50 to 500 mg of active ingredient per unit dosage form.

In one embodiment, when the active ingredient needs to enter circulation and be delivered via blood, the active ingredient, can be administered to achieve peak plasma concentrations of the active compound of from about 0.5 to about 75 µM, about 1 to 50 µM, and about 2 to about 30 µM. This may be achieved, for example, by the intravenous injection of a 0.05 to 5% solution of the active ingredient, optionally in saline, or orally administered as a bolus containing about 1-100 mg of the active ingredient.

Desirable blood levels may be maintained by continuous infusion to provide doses at a particular mg/kg/hr or by intermittent infusions containing a selected amount (mg/kg) of the active ingredient(s).

The desired dose may conveniently be presented in a single dose or as divided doses administered at appropriate intervals, for example, as two, three, four or more sub-doses per day or per procedure. The sub-dose itself may be further divided, e.g., into a number of discrete loosely spaced administrations.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

The present invention further provides kits. Kits of the invention comprise at least one compound of the invention and an instructional material for the use thereof, and optionally an applicator.

The invention also includes a kit comprising a composition of the invention, optionally cells, a compounds of the invention, and an instructional material which describes administering or using the composition or the cells. In another embodiment, this kit comprises a (preferably sterile) solvent suitable for dissolving or suspending the composition of the invention prior to administering the composition. Optionally, at least one growth factor and/or antimicrobial agent may be included in the kit.

Examples

Methods
Fish Husbandry

All animal studies were approved by the University of Virginia Institutional Animal Care and Use Committee. Zebrafish strains used in this study were: AB*, Tg(sox10 (4.9):eos) (Prendergast et al., 2012), Tg(olig2:egfp)$^{vu12}$, Tg(olig2:dsred)$^{vu19}$ (Shin et al., 2003), Tg(nkx2.2a: megfp)$^{vu17}$ (Kucenas et al., 2008b), Tg(mbp:egfp-CAAX) (Almeida et al., 2011), adora2aa$^{ct845}$ and gpr126$^{st49}$ (Monk et al., 2009). Table 1 denotes abbreviations used for each strain and summarizes what each transgene labels. Embryos were raised at 28.5° C. in egg water and staged by hours or days post fertilization (hpf and dpf, respectively). Embryos of either sex were used for all experiments (Kimmel et al., 1995). Phenylthiourea (PTU) (0.004%) in egg water was used to reduce pigmentation for imaging. Stable, germline transgenic lines were used in all experiments with the exception of the F0 CRISPR data.

Chemical Treatments

The LOPAC®$^{1280}$ library (Sigma Cat. No. LO1280) was used for the chemical screen. 384 well masterplates, a gift from Drs. John Lazo and Elizabeth Sharlow, were replated and diluted with DMSO to create 1 mM 96-well stock plates. At 24 hours post fertilization (hpf), olig2:dsred embryos were dechorionated using 0.2% pronase. Embryos remained in pronase for 2 minutes at 25° C. and were washed 4 times with egg water at 25° C. One embryo was placed in each well of a 96 well plate with 198 µl of water. 2 µl of compound from the 96 well stock plate was added to the water for a final concentration of 10 µM compound and 1% DMSO. For the initial screen, we tested each drug once in 1 well of a 96 well plate. Each row of the plate also contained 1 positive and 1 negative control well. 4 µM AG1478 was used as a positive control and 1% DMSO was used as a negative control for each plate. Plates were covered with a low evaporation lid and placed in a 28.5° C. incubator until analysis at 72 hpf. Plates were analyzed on a Zeiss AxioObserver inverted microscope equipped with epifluorescence using a 10× objective (NA=0.3). At 72 hpf, the presence or absence of peripheral olig2$^+$ cells was scored for each larva. All positive hits from the primary screen were retested on 3 embryos in a secondary screen in which LOPAC®$^{1210}$ compounds, AG1478, and 1% DMSO treatments were randomized across the plate and all experimenters were blinded to the identity of compounds or controls until after analysis. Any experiment in the secondary screen in which fewer than 8 positive control embryos or greater than one DMSO treated embryo had ectopic OPCs was excluded and later repeated. For all subsequent drug experiments, new chemical stocks were obtained from suppliers, and embryos were manually dechorionated using forceps. 1% DMSO was used as a negative control for all drug treatment experiments, except carbenoxolone and MK-801, which were dissolved in distilled water. Using the same microscope and objective as in the original screen, we quantified peripheral olig2$^+$ cells for whole larvae, excluding the first (anterior) 2 somites which are obscured by the yolk, and the last (posterior) 4 somites in the tail, which develop more slowly than the rest of the trunk.

In Vivo Imaging

Embryos were anesthetized with 0.01% 3-aminobenzoic acid ester (Tricaine), immersed in 0.8% low-melting point agarose and mounted laterally in glass-bottomed 35 mm petri dishes (Electron Microscopy Sciences). After mounting, the petri dish was filled with egg water containing PTU and Tricaine. For some experiments, chemical compounds were also dissolved in the water. A 25× multi-immersion objective (NA=0.8), 40× oil objective (NA=1.4) and a 40× water objective (NA=1.1) mounted on a motorized Zeiss AxioObserver Z1 microscope equipped with a Quorum WaveFX-XI spinning disc confocal system (Quorum Technologies Inc.) were used to capture images. Image processing was performed with MetaMorph and Photoshop to enhance brightness and contrast of images. The Fiji plugin MTrackJ was used to annotate time-lapse movies (Meijering et al., 2012).

We used fate mapping with photoconversion of the sox10:eos transgenic line to identify MEP glia in some experiments. The nascent Eos protein exists in a green fluorescent state, but when exposed to ultraviolet (UV) light, it permanently shifts to a red fluorescent state. When exposed to UV light at 48 hpf, neural crest-derived cells are photoconverted to red fluorescence. MEP glia, which are not neural crest-derived and begin expressing sox10:eos after 48 hpf, are not photoconverted and can be identified as GFP$^+$ cells on the nerve root (Smith et al., 2014). For photoconversion, the entire trunk of sox10:eos larvae was exposed to 30 seconds of UV light through a DAPI filter using a 20× objective (NA=0.8).

Immunohistochemistry and Fluorescent Antagonist Treatment

Embryos were fixed and stained using the procedure previously described (Smith et al 2014). Antibodies used were: rabbit anti-A2a (1:100 GeneTex (Andersson et al., 2012)), rabbit anti-Sox10 (1:5000 (Binari et al., 2013)), rabbit anti-MBP (1:250 (Kucenas et al., 2009)), and Alexa 647 goat anti-rabbit (1:600) (ThermoFisher). Fluorescent SCH-58261 (SCH-red) was purchased from CisBio. 25 hpf embryos were immersed in 7.14 µM SCH-red in 30% DMSO for 30 minutes, then fixed in 4% PFA at 25° C. for 3 hours. Embryos were mounted in glass-bottomed petri dishes for imaging as described above.

Morpholino and mRNA Injections

Antisense morpholino oligonucleotides (MO) were purchased from Gene Tools. adora2aa$^{MOI}$ (Haas et al., 2013) is complementary to the region spanning the translation start codon of adora2aa mRNA, and adora2ab$^{MOI}$ is complementary to the region immediately 5' to the start codon of adora2ab mRNA. Embryos were injected with 2 to 3 nl of injection solution (distilled water, 4 mg/ml phenol red, diluted MO) at the 1-cell stage. Any embryos damaged during the injection procedure were removed, and the rest were incubated at 28.5° C. Data presented for each MO are combined from at least 3 independent experiments. Uninjected controls and phenol red control injections were performed at least twice for each data set.

For Tetanus Toxin experiments, TeNT cDNA was prepared from plasmid pGEMTEZ-TeTxLC (a gift from Marcel Tawk) as previously described (Fontenas et al., 2016). TeNT mRNA was prepared using the mMessage mMachine SP6 in vitro transcription kit (ThermoFisher). Injections of mRNA encoding Tetanus Toxin Light Chain (TeNT) were performed at the 1 to 2 cell stage. A 2 nl volume of 175 ng/μl mRNA in DEPC-treated distilled water was used. All embryos were manually dechorionated at 2 dpf and evaluated for paralysis at that time. The startle reflex was also analyzed at 3 dpf as further evidence that TeNT expression caused inhibition of neuronal firing.

Adora2ab CRISPR Injections sgRNA targeting adora2ab was designed using CHOPCHOP (see the ChopChop website) and a protocol previously described (Gagnon et al., 2014). The sgRNA target for solute carrier family 45 member 2 (slc45a2) has been previously published (Irion et al., 2014). The sgRNA target for tyrosinase (tyr) has been previously published (Jao et al., 2013). We annealed the 5' gene-specific oligo and the 3' constant oligo using the PCR protocol described in (Nakayama et al., 2014). We transcribed sgRNA using Ambion Megascript T7 kit and injected 2 nl of 200-400 ng/μl sgRNA with 500 ng/μl Cas9 protein (PNA Bio) dissolved in nuclease-free water into cells of olig2:dsred or olig2:egfp embryos at the 1 cell stage. Larvae were analyzed at 3 dpf for peripheral OPCs and then DNA was extracted from individual larvae for sequencing. Primers were used to PCR amplify a 279 base pair region of genomic adora2ab, and Sanger sequencing with a primer was used to identify CRISPR-induced mutations. Sequence trace files were analyzed with ApE or SnapGene. Because mutations are mosaic in F0 animals, we cloned single mutated DNA fragments using TOPO cloning. To analyze the CRISPR induced-mutations, DNA from 3 dpf individual embryos was extracted and amplified by PCR using the adora2ab forward and reverse primers. PCR was done with GoTaq green master mix (Promega) and conditions were as follows: 95° C. for 3 min, followed by 35 cycles at 95° C. for 30 s, 60° C. for 30 s and 72° C. for 1 min. Final extension was at 72° C. for 20 min. PCR products from individual embryos were TOPO TA cloned into pCR8/GW vectors (Invitrogen). For each embryo, 8 clones were sequenced using the M13 forward primer. Sequences were aligned to WT genomic DNA using BLAST global alignment tool. All F0 CRISPR data presented in this manuscript has been confirmed via sequencing and the gRNAs have been verified to induce reproducible cuts within the target gene (Table 2).

Creation of adora2aa Mutant Line

A TALEN targeting zebrafish adora2aa was designed using the ZiFIT Targeter (see ZiFIT website) (Sander et al., 2011) and constructed as previously described (Chen et al., 2013). TALEN mRNA was synthesized from purified linear DNA using the mMessage mMachine T7 Ultra kit (Ambion); 50-100 μg of TALEN mRNA dissolved in nuclease-free water was injected into zebrafish embryos at the 1-cell stage. To identify founders, injected embryos were raised to adulthood and mated, then genomic DNA was isolated from a pool of 1 to 6 embryos from each potential founder. PCR was performed using primers, and indels were identified by analyzing PCR product sizes using Peak Scanner (Applied Biosystems). To confirm indel sequences, genomic DNA from single embryos was amplified and subcloned using the Strataclone PCR Cloning Kit (Stratagene), and DNA sequences were then analyzed with SeqBuilder and SeqMan (DNAStar Lasergene).

Genotyping

Genomic DNA was extracted using HotSHOT (hot sodium hydroxide and tris) (Truett et al., 2000). The primers used for genotyping gpr126$^{st49}$ have previously been published (Monk et al., 2009). Primers were used to amplify a 151 bp product within adora2aa. Because the mutation is a 7 bp deletion and is difficult to resolve on an agarose gel, we performed Sanger sequencing using a primer to identify WT, heterozygous, and homozygous mutants.

In Situ Hybridization and Sectioning

Larvae were fixed in 4% PFA at 4° C. overnight and stored in 100% methanol at −20° C. and processed for in situ RNA hybridization. Plasmids were linearized with appropriate restriction enzymes and cRNA preparation was carried out using Roche DIG-labeling reagents and RNA polymerases (NEB). We used a previously published probe for wif1 (Smith et al., 2014). After in situ hybridization, embryos were embedded in 1.5% agarose/30% sucrose and frozen in 2-methylbutane chilled by immersion in liquid nitrogen. We collected 20 μm transverse sections on microscope slides using a cryostat microtome and covered with 75% glycerol. Images were obtained using a Zeiss AxioObserver inverted microscope using a 40× oil immersion objective. All images were imported into Adobe Photoshop. Adjustments were limited to levels, contrast, and cropping.

Statistics

GraphPad Prism was used for all statistical analyses. Unpaired student's t-test or, for multiple comparisons, 1-way ANOVA followed by Bonferonni post test, were used for quantifications of OPCs, MEP glia, Eos$^+$ peripheral cells, A2a antibody expression, and heart rate. Chi-squared analysis was used for quantification of paralysis and startle reflex, and survival test was used for analyzing mutant survival and hatching. A p value less than 0.05 was considered statistically significant. For dose response experiments, 10 to 12 embryos were treated per dose, and n is reported as the range of larvae analyzed per dose. To quantify A2a antibody expression, a region of interest was drawn around the spinal motor and sensory nerve roots using ImageJ, and integrated density was calculated for this region of interest. To correct for background fluorescence, integrated density was calculated for an identical region of interest adjacent to the nerve roots, and this value was subtracted from the nerve root value to achieve the corrected total fluorescence for each nerve root.

Results

Identification of Molecules that Induce Ectopic OPC Migration Through the MEP TZ Glial cells that establish a barrier to OPC migration across the MEP TZ have been identified in mice and fish (Coulpier et al., 2010; Frob et al., 2012; Smith et al., 2014). In zebrafish, MEP glia positioned at the motor root axons prevent OPCs from migrating out of the spinal cord (Smith et al., 2014). During development, ventral OPCs within the spinal cord extend membrane processes through the MEP TZ and contact MEP glia (FIG. 1A). When this occurs, the OPC is immediately repelled and retracts its process. When MEP glia are absent, OPCs freely migrate through the MEP TZ and onto peripheral motor nerves (Morris et al., 2017; Smith et al., 2014). However, the signals restricting OPC migration at the MEP are unknown. Therefore, to identify molecular mechanisms regulating OPC migration at the MEP TZ, we conducted an unbiased screen of pharmacologically active compounds to identify signaling cascades involved in OPC segregation to the CNS.

To conduct our screen, we treated olig2:dsred embryos, which express DsRed in motor neurons and OPCs, at 24 hours post fertilization (hpf) with compounds from the Library of Pharmacologically Active Compounds (LOPAC®$^{1280}$). In a primary screen, one or two embryos per well of a 96 well plate were treated with either 10 µM of a compound from the library, 1% DMSO as a negative control, or 4 µM AG1478 as a positive control (FIG. 1$i$). The positive control AG1478 inhibits Erbb3 signaling and phenocopies the erbb3b mutation (Lyons et al., 2005). Previously, we demonstrated that erbb3b mutants have peripherally-migrated OPCs because they lack MEP glia (Morris et al., 2017; Smith et al., 2014). A pilot experiment confirmed that treatment with 4 µM AG1478 from 24 to 72 hpf caused robust peripheral OPC migration, whereas 1% DMSO did not (FIG. 1C). For the rest of our screen, we analyzed larvae at 72 hpf for the presence of olig2$^+$ cell bodies in the periphery (FIG. 1C). Any compound resulting in at least one peripheral olig2$^+$ cell per larva was considered a positive "hit". 197 hits were found in our primary screen, with 910 compounds having no peripherally-migrated olig2$^+$cells, and the remaining 173 compounds resulted in death of the embryo. All hits from the primary screen were retested in a secondary screen using the same protocol but with the following modifications: 1) each compound was tested in triplicate, 2) all compounds, including 12 positive and 12 negative controls, were randomized across the plate and 3) we were blinded to which wells contained experimental compounds or controls until after analysis (FIG. 1D). Any compound resulting in at least one peripheral olig2$^+$ cell in 3/3 or 2/2 (if one sample died) larvae was considered a validated hit (FIG. 1E). This screening protocol resulted in 11 total validated hits, and 10 out of those 11 compounds resulted in multiple peripheral OPCs per larva. Table 1 describes all of the validated compounds. One of the 11 compounds was removed from the final list in Table 1 because an independent stock from the supplier did not reproduce the same ectopic OPC migration phenotype observed in the screen. Intriguingly, from this screen, we discovered multiple compounds involved in neurotransmission and/or modulation of neuronal activity (Table 1). For the remainder of this manuscript, we will focus on one signaling cascade identified in this screen. We focused further testing on one of these compounds, an adenosine receptor (AR) antagonist, because adenosine is a well-known modulator of neuronal activity, and neuronal activity has been implicated in regulating OPC differentiation, proliferation, and migration (Gibson et al., 2014; Stevens et al., 2002).

A2a ARs Mediate OPC Migration at the MEP TZ

One compound we identified, CGS-15943, is a highly potent, non-selective AR antagonist (Ongini et al., 1999). Adenosine is a well-known modulator of neuronal activity and can either increase or decrease neuronal firing by binding to different ARs (Sebastiao and Ribeiro, 2015). Because adenosine can modulate neuronal activity, and purinergic signaling has been implicated in OL differentiation and migration (Dennis et al., 2012; Stevens et al., 2002) we focused our experiments on this cascade.

Figure 2A:
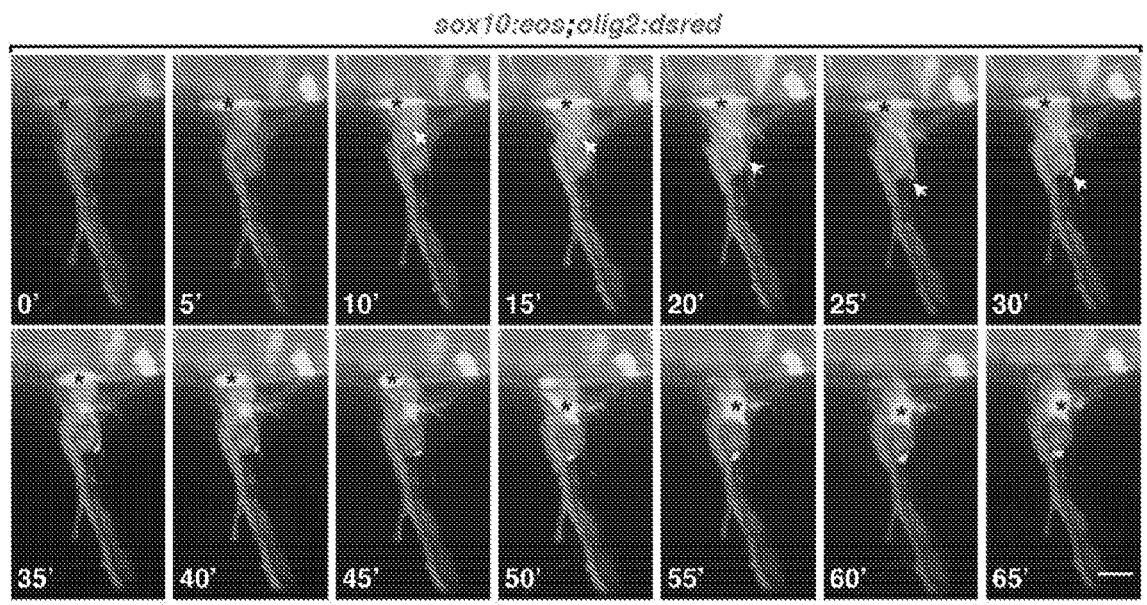
FIG. 2 comprises FIG. 2A-2E. AR antagonists cause OPC migration through the MEP TZ. (A) Frames captured from a 15 hour time-lapse movie of a sox10:eos;olig2:dsred larvae treated with CGS-15943 from 24 to 72 hpf and imaged from 57 to 72 hpf 0' is 58 hpf. Black asterisk marks OPC cell body. Arrowhead marks OPC leading process. (B-C) Peripheral OPC counts for fish treated from 24 to 72 hpf with CGS-15943 or SCH-58261. Mean±SEM, n=9-10 larvae per dose. (D) Mean±SEM of peripheral OPCs in olig2:dsred larvae treated with 10 µM SCH-58261 alone or in combination with 2.5 µM CGS-21680 or 5 µM adenosine from 36 to 72 hpf. n=29-30 fish per treatment. (E) Peripheral OPC counts for larvae treated with 10 µM SCH-58261 during distinct developmental periods. Green bars indicate mean peripheral OPC counts significantly above DMSO control (p<0.05), and red bars indicate mean peripheral OPC counts not significantly different than DMSO (p>0.05) n=9-12 larvae per condition. * p<0.05, ** p<0.01 compared to DMSO. Scale bar, 20 µM.

We first confirmed that CGS-15943 caused peripheral OPC migration through the MEP TZ by performing in vivo, time-lapse imaging. In order to distinguish OPCs from motor neurons, we used embryos expressing olig2:dsred and sox10:eos, where sox10 regulatory elements drive expression of Eos in central and peripheral glia. OPCs appear Eos$^+$ and DsRed$^+$ (yellow). We treated these embryos with 10 µM of CGS-15943 from 24 to 72 hpf and imaged 3 larvae (10 nerves total) from 55 to 72 hpf. In these time-lapse movies, we observed sox10$^+$/olig2$^+$ cells with highly dynamic membrane processes at the MEP TZ (FIG. 2A). Because of the morphology, behavior, and co-expression of olig2 and sox10, we confirmed that they were OPCs. In 9 out of 10 nerves imaged, we observed OPCs extend highly dynamic membrane processes through the MEP TZ. On 6 out of 10 nerves, OPC cell bodies squeezed through this opening and migrated onto peripheral spinal motor nerves during imaging (FIG. 2A). This migration most often occurred between 60 and 72 hpf, although we sometimes observed OPCs already present on the nerve before 60 hpf (3 out of 10 nerves). We never observed more than 2 OPCs migrate through a single MEP TZ, and these cells stayed closely associated with the motor nerve for the duration of imaging. Interestingly, we never observed any olig2$^+$/sox10$^-$ motor neurons in the periphery in these time-lapse movies (0 out of 10 nerves), indicating that adenosine signaling is necessary for restricting OPCs to the spinal cord, but not motor neurons. This is consistent with evidence from our lab and others demonstrating that distinct mechanisms regulate segregation of glia and neurons at the MEP TZ (Frob et al., 2012; Kucenas et al., 2009).

Figure 2B:
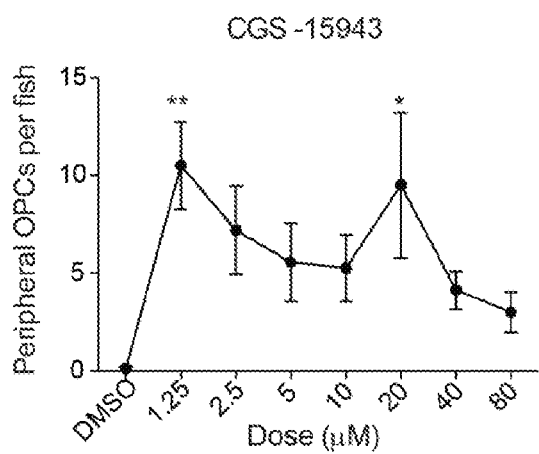
Figure 2C:
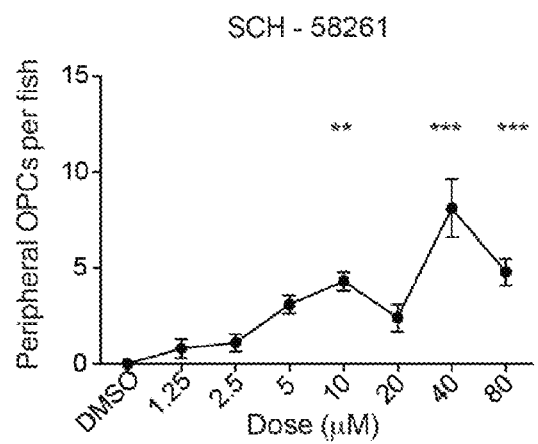
Figure 8C:
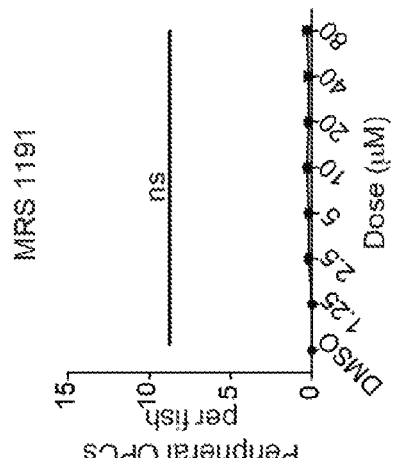
Figure 8B:
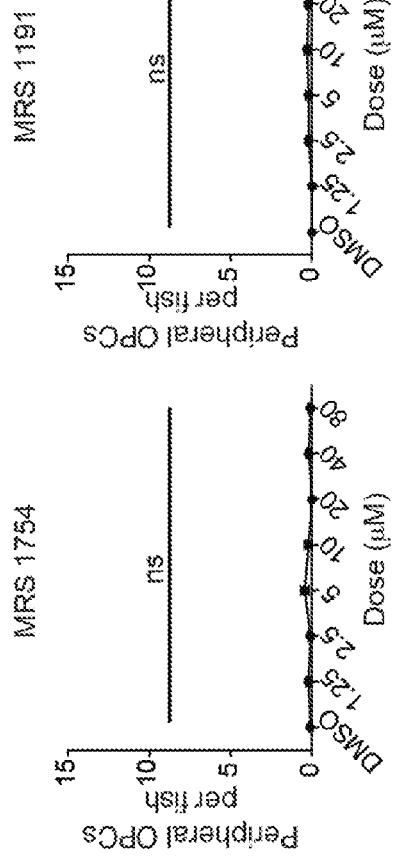
Figure 8A:
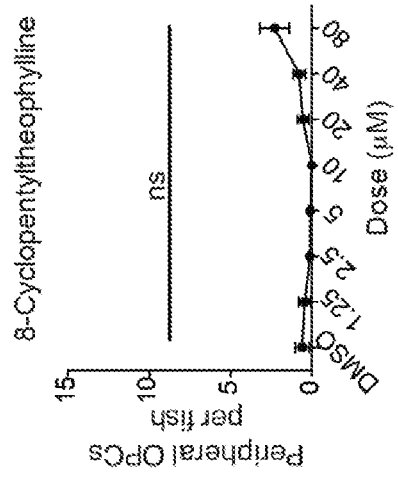
Figure 8F:
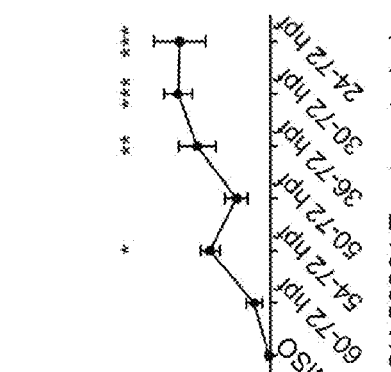
Figure 8E:
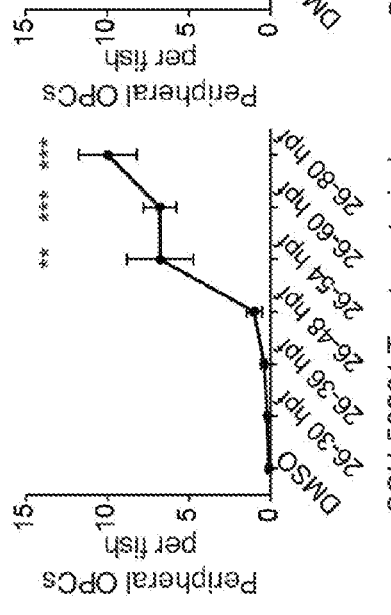
Figure 8D:
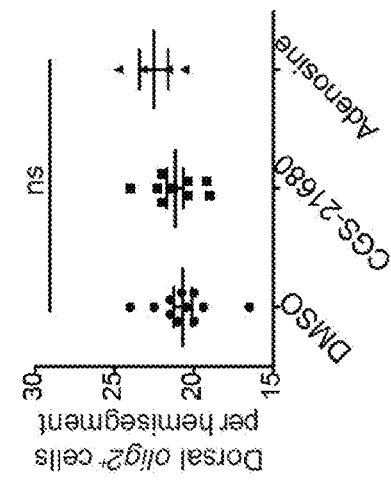
Figure 8G:
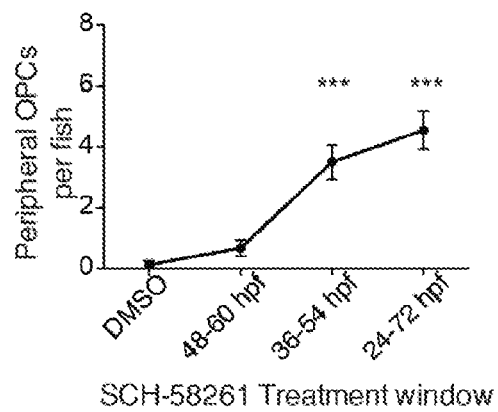

We next sought to determine which AR subtype was required for preventing peripheral OPC migration. To do this, we treated embryos expressing olig2:dsred from 24 to 72 hpf with selective antagonists for each of the 4 AR subtypes: A1 (8-cyclopentyltheophylline (CPT), n=9-10 embryos per dose), A2a (SCH-58261, n=10 embryos per dose), A2b (MRS-1754, n=10 embryos per dose), and A3 (MRS-1191, n=10 embryos per dose), as well as the general AR antagonist, CGS-15943 (n=5-10 embryos per dose) (Jiang et al., 1996; Ongini et al., 1999; Searl and Silinsky, 2012; Wei et al., 2013). We analyzed drug-treated larvae at 3 days post fertilization (dpf) using the same methods described for the original chemical screen, and quantified the number of peripheral olig2$^+$ OPCs. As expected, CGS-15943 caused significant peripheral OPC migration at doses of 1.25 and 20 µM (FIG. 2B, p<0.01). This confirmed the qualitative results from our screen and time-lapse data that AR antagonism results in peripherally-migrated OPCs. The selective A2a AR antagonist, SCH-58261, also resulted in significant numbers of peripheral olig2$^+$ OPCs (FIG. 2C, p<0.01 for 10 µM SCH-58261 compared to DMSO), whereas we did not observe peripheral OPCs following treatment with selective antagonists for any of the other AR subtypes (FIGS. 8A-8C). From these data, we conclude that only A2a ARs are involved in regulating OPC migration at MEP TZs. Therefore, we performed all subsequent experiments using SCH-58261 at 10 µM, as this dose had the most robust effect on OPC migration without causing toxicity to the larvae.

We sought to further confirm the selectivity of SCH-58261 activity to A2a ARs with competitive binding experiments. If SCH-58261 selectively antagonizes the A2a AR to disrupt OPC migration, we hypothesized that co-administering an A2a agonist would rescue the peripheral migration phenotype caused by SCH-58261. To test this, we treated 24 hpf olig2:dsred embryos with 10 µM SCH-58261 combined with 5 µM adenosine or 2.5 µM of the A2a selective agonist, CGS-21680 and quantified the number of peripheral OPCs at 3dpf (Jarvis and Williams, 1989). Both adenosine and CGS-21680 significantly decreased the number of peripheral OPCs when co-administered with SCH-58261 (FIG. 2D, p<0.05 CGS-21680; p<0.01 adenosine compared to SCH-58261 alone, n=29-30 larvae). These results support the conclusion that SCH-58261 selectively antagonizes A2a ARs to induce ectopic OPC migration, and this effect can be mitigated with A2a AR agonists. To confirm that adenosine or CGS-21680 treatment alone did not interfere with normal OPC development or migration within the spinal cord, we imaged olig2:dsred zebrafish larvae at 3 dpf following treatment with adenosine, CGS-21680, or DMSO from 24 to 72 hpf and quantified dorsal spinal cord olig2$^+$ OPCs in a 4-somite region and did not observe any differences among treatments (FIG. 8D, p=0.23; adenosine, n=4 larvae; CGS-21680, n=9 larvae; DMSO, n=11 larvae).

In our initial screen, our treatment protocol spanned from 24 to 72 hpf, encompassing OPC specification, proliferation, and migration (Kirby et al., 2006; Kucenas et al., 2008; Park et al., 2002). We sought to narrow the treatment window to see if A2a AR signaling was sufficient while OPCs were actively migrating. To do this, we treated olig2:dsred embryos with 10 µM SCH-58261 during various time windows and quantified the number of peripheral OPCs at 3 dpf. We found that exposure to SCH-58261 beginning later than 54 hpf or ending earlier than 54 hpf did not result in any peripheral OPC migration (FIG. 2E and FIGS. 8E-G, n=7-12 larvae). At this stage, OPCs are migrating throughout the spinal cord and we previously observed OPCs extending membrane processes into the periphery and contacting MEP glia during this time window (Kirby et al., 2006; Smith et al., 2014). In subsequent experiments, we began treatments at 36 hpf since earlier treatment did not significantly increase the number of peripheral OPCs observed in the periphery. We conclude from these experiments that adenosine signaling is necessary when OPCs begin migrating, but not during their specification, to prevent them from migrating into the PNS.

A2a AR Antagonists do not Disrupt Spinal Motor Nerve Development

Figure 3B:
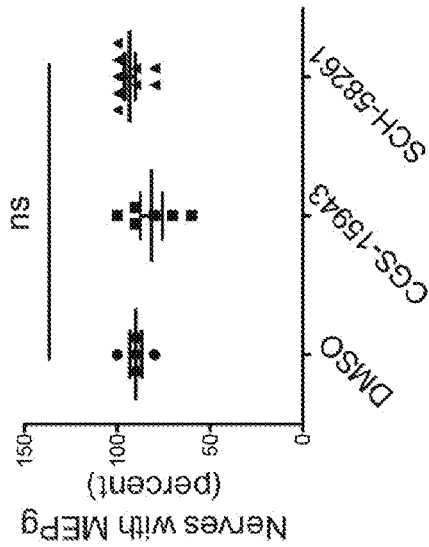
FIG. 3 comprises FIGS. 3A-3D. A2a AR antagonism does not affect spinal motor nerve development. (A) Motor nerve in a 72 hpf olig2:dsred;sox10:eos larvae treated with DMSO from 36 to 72 hpf. Asterisk marks sox10$^+$/olig2$^+$ MEP glia with normal morphology at the MEP. (B) Mean±SEM of the percent of nerves per larva at 72 hpf with sox10$^+$/olig2$^+$ MEP glia after treatment from 36 to 72 hpf with DMSO (n=5), CGS-15943 (n=6), or SCH-58261 (n=9). Ten (10) nerves were quantified per larva. p=0.14 (C) 55 hpf nkx2.2a:megfp;olig2:dsred larvae treated with DMSO or CGS-15943 from 36 to 55 hpf showing PG extension on the nerve. (D) Quantification of Eos$^+$ cells per nerve at 72 hpf in DMSO and SCH-58261-treated larvae. Mean±SEM for n=6 fish, 10 nerves per fish, p=0.08. Scale bars, 20 µM.

Previously, we demonstrated that loss of MEP glia resulted in OPC migration into the periphery (Morris et al., 2017; Smith et al., 2014). We therefore sought to determine whether antagonizing the A2a AR lead to ectopic OPC migration simply by perturbing MEP glial development. MEP glia can be identified by the co-expression of sox10: eos and olig2:dsred as well as expression of wnt inhibitory factor 1 (wif1) (Smith et al., 2014). To determine if MEP glia were present in larvae treated with the A2a AR antagonist, we quantified the percentage of motor nerves with sox10$^+$/olig2$^+$ MEP glia at the MEP TZ and observed no differences among larvae treated from 36 to 72 hpf with 1.25 µM CGS-15943 (n=6 larvae), 10 µM SCH-58261 (n=9 larvae) or DMSO (n=5 larvae) (FIGS. 3A and 3B p=0.14, 10 nerves analyzed per larvae). We also observed wif1$^+$ MEP glia in larvae treated with 1.25 µM CGS-15943 (FIG. 9). From these data, we conclude that A2a AR antagonism does not affect MEP glial development.

Figure 3D:
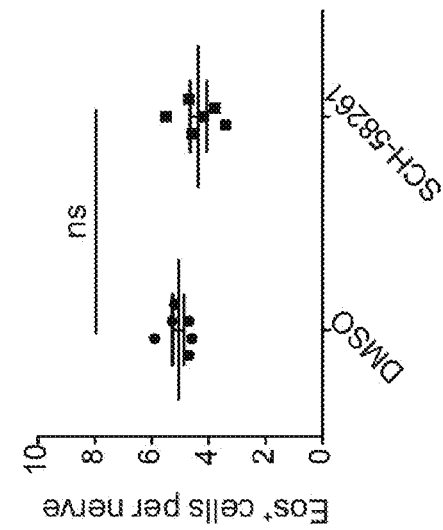
Figure 3A:
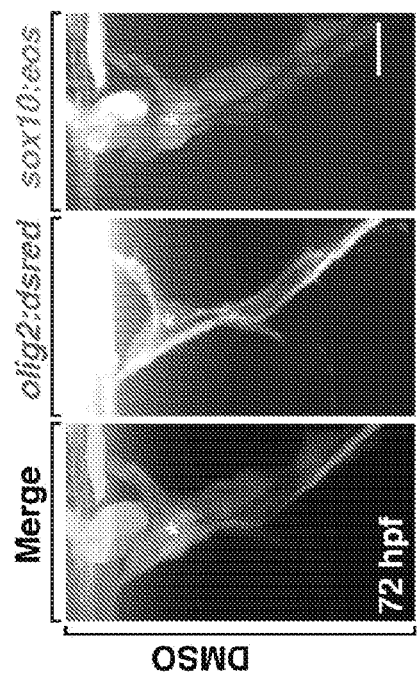
Figure 3C:
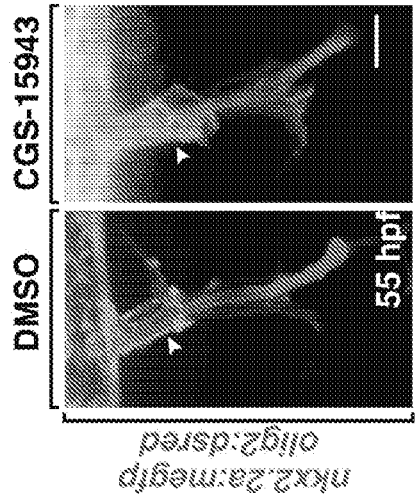

To determine whether glial migration in general was disrupted at the MEP TZ in larvae treated with the A2a AR antagonist, we assayed the migration of perineurial glia (PG). These cells originate in the ventral spinal cord, exit the CNS via the MEP TZ, and migrate along motor nerves to form the perineurium, a component of the blood-nerve-barrier (Kucenas et al., 2008). If the A2a AR antagonist nonselectively disrupted cell migration at the MEP TZ, we would expect to see altered migration of PGs. We measured extension of PG from the spinal cord along the motor nerve in 55 hpf nkx2.2a:megfp;olig2:dsred larvae treated from 36 to 55 hpf with 1.25 µm CGS-15943, where nkx2.2a regulatory sequences drive membrane-tethered GFP in PG. We found no difference in PG extension between DMSO-treated and CGS-15943-treated larvae, indicating that A2a AR signaling is specifically required to regulate OPC migration and does not generally affect glial migration at the MEP TZ (FIG. 3C, p=0.28; DMSO 22.27±0.88 µm (mean SEM) n=6 larvae, 10 nerves analyzed per larva; CGS-15943 24.94±1.75 µm (mean SEM) n=10 larvae, 10 nerves analyzed per larva). Finally, we quantified the number of Schwann cells (SC) and MEP glia on motor nerves as a measure of overall nerve health. Using 72 hpf sox10:eos larvae, where sox10 drives expression of Eos in SCs and MEP glia in the PNS, we quantified the number of Eos$^+$ cells between the MEP TZ and horizontal myoseptum on 10 nerves per larva, for n=6 larvae per treatment. In these studies, we observed that the number of Eos$^+$ cells per nerve was not significantly different between animals treated from 36 to 72 hpf with DMSO or SCH-58261 (p=0.08) (FIG. 3D). From these experiments, we conclude that the A2a AR antagonist, SCH-58261, does not cause peripheral OPC migration by nonselectively stimulating glial migration or by perturbing MEP glial development. Therefore, we conclude that antagonizing A2a ARs specifically affects OPC migration.

The A2ab AR Regulates OPC Migration

Zebrafish have two orthologous A2a ARs, A2aa and A2ab, which are encoded by adora2aa and adora2ab, respectively (Boehmler et al., 2009). We used Clustal Omega to compare the zebrafish A2aa, A2ab, and human A2A AR protein sequences (Goujon et al., 2010; Sievers et al., 2011). The ligand binding domains of zebrafish A2aa and A2ab ARs are 72% (21/29) conserved with human A2A AR, and A2aa and A2ab ARs have 76% (22/29) conserved amino acids with each other in this domain, so they likely have similar ligand affinities (data not shown). However, adora2aa and adora2ab have distinct expression patterns, so we hypothesized that they may have unique functions in nervous system development (Boehmler et al., 2009).

To determine if A2aa and/or A2ab ARs were required to prevent peripheral OPC migration, we used a combination of genetic mutants and knock-down strategies. We created germline mutations in adora2aa using transcription activator-like effector nuclease (TALEN) targeted mutagenesis (Boch et al., 2009; Moscou and Bogdanove, 2009). adora2aa$^{ct845}$ is a 7 base pair (bp) deletion within exon 3, causing a frameshift and an early stop codon, and this results in a severely truncated protein sequence (data not shown). The mutated A2aa AR protein lacks transmembrane domains 6 and 7, which contain conserved ligand binding residues (de Lera Ruiz et al., 2014). It also lacks the entire C-terminal cytoplasmic tail, which mediates interaction with G proteins and protects the receptor from ubiquitination and degradation (Keuerleber et al., 2010). For these reasons, we hypothesize that adora2aa$^{ct845}$ is a presumptive null. Similar to A2a$^{-/-}$ mice, adora2aa$^{-/-}$ zebrafish mutants are homozygous viable, produce viable offspring and do not show any morphological defects compared to WT siblings at all stages investigated (FIG. 10A-F); survival and hatching n=50; heart rate n=20; startle mutants n=25, WT n=34) (Chen et al., 1999).

Figure 10A:
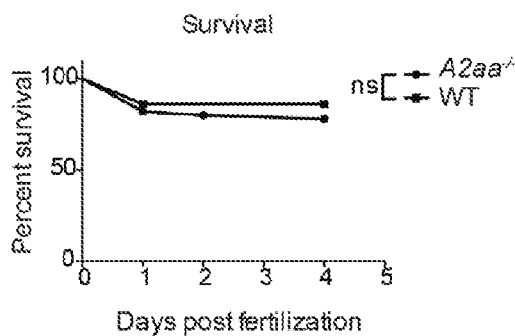
Figure 10B:
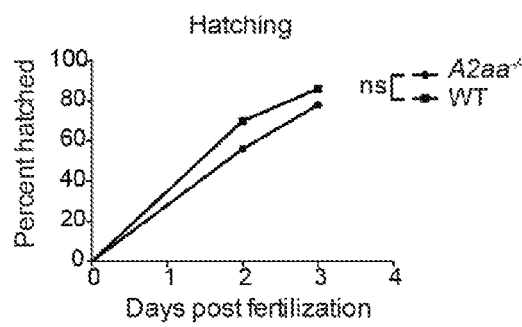
Figure 10C:
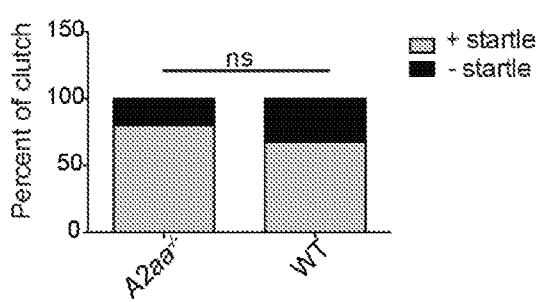
Figure 10D:
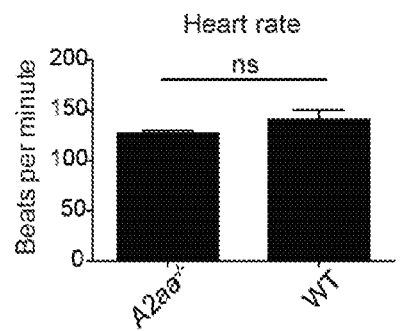
Figure 10E:
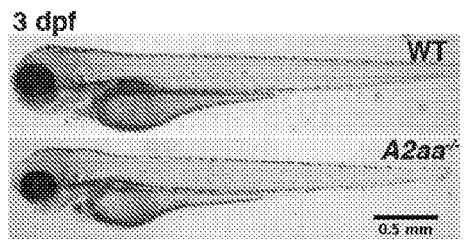
Figure 10F:
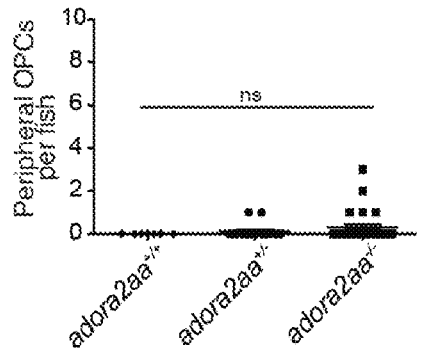

To determine if adora2aa mediated OPC restriction from the PNS, we quantified the number of peripheral OPCs at 3 dpf in olig2:dsred larvae with adora2aa mutations (FIG. 10F). At this stage (n=7 adora2aa$^{+/+}$, n=20 adora2aa$^{+/-}$, n=26 adora2aa$^{-/-}$), we did not observe significant numbers of peripheral OPCs in adora2aa$^{-/-}$ mutants (p=0.69). Based on this result, we concluded that A2aa ARs were likely not involved in regulating OPC migration and that the effect of the A2a AR antagonist on ectopic OPC migration may be working through A2ab ARs.

Figure 4A:
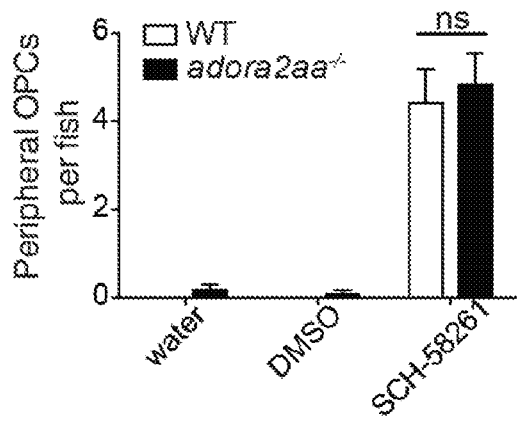
FIG. 4 comprises FIG. 4A-4G. A2ab ARs mediate OPC migration at the MEP TZ. (A) Mean±SEM of peripheral OPCs per fish for olig2:dsred;adora2aa$^{-/-}$ and WT larvae treated with water, DMSO or 10 µM SCH-58261 from 36 to 72 hpf n=12 fish, p<0.0001 for Treatment, p=0.53 for Genotype, p=0.93 for Interaction of Treatment and Genotype. (B) Mean±SEM of peripheral OPCs at 3 dpf in WT olig2:dsred embryos injected with vehicle, 1 ng/nl adora2aa$^{MOI}$ or 1 ng/nl adora2ab$^{MOI}$. n=42 (WT), 11 (phenol red), 65 (adora2aa$^{MOI}$), 42 (adora2ab$^{MOI}$), * p<0.0001 adora2ab$^{MOI}$ compared to WT. (C) Mean±SEM of peripheral OPCs at 3 dpf in olig2:dsred;adora2aa$^{-/-}$ larvae injected with adora2ab$^{MOI}$. n=44 (uninjected), n=30 (phenol red), n=84 (adora2ab$^{MOI}$), * p<0.0001 compared to uninjected. (D) Quantification of A2a antibody at the nerve root of WT, adora2aa$^{MOI}$, or adora2ab$^{MOI}$ injected larvae. Mean±SEM *** p<0.0001 compared to WT, n=20 nerves (WT), 59 nerves (adora2aa$^{MOI}$), 80 nerves (adora2ab$^{MOI}$). (E,F,G) Lateral views of 3 dpf olig2:dsred WT or CRISPR FO injected larvae. Arrowheads mark peripheral OPCs in FO larvae. Scale bar, 25 µm.

We tested this hypothesis by treating olig2:dsred; adora2aa$^{-/-}$ mutants, which still have functional A2ab ARs, with the A2a AR antagonist, SCH-58261, at 36 hpf. At 72 hpf, we did not observe peripherally-migrated OPCs in WT or adora2aa$^{-/-}$ mutants treated with DMSO (FIG. 4A, n=12). However, when WT or adora2aa mutants were treated with SCH-58261 from 36 to 72 hpf, we observed peripheral OPCs in both genotypes (FIG. 4A, n=12). Two-way ANOVA analysis showed a significant effect of drug treatment (p<0.0001), but not for genotype (p=0.53) or the interaction between treatment and genotype (p=0.93). In other words, both WT and adora2aa mutant larvae have the same number of peripherally-migrated OPCs when treated with the A2a AR antagonist. These results are consistent with the hypothesis that A2ab, and not A2aa, is primarily responsible for affecting OPC migration.

Figure 4B:
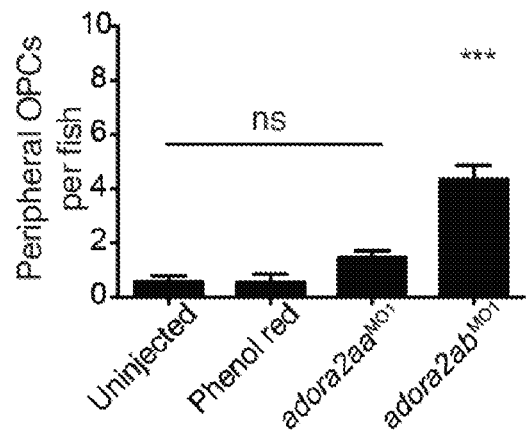
Figure 4C:
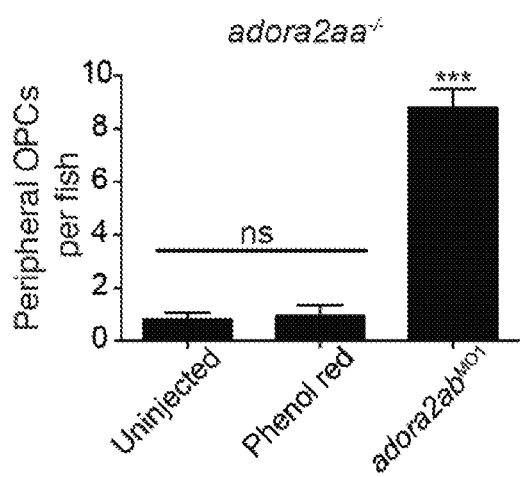

To further confirm the roles of the two orthologous receptors, we used morpholino oligonucleotides (MO) to selectively knock down expression of adora2aa and adora2ab. A translation blocking adora2aa$^{MOI}$ has been previously described (Haas et al., 2013). To create the translation blocking adora2ab$^{MOI}$, we used the Oligo Design service at Gene Tools (see their website). We first titrated the concentration of injected MO in order to minimize the risk of off-target effects and observed that 1 ng/nl adora2ab$^{MOI}$ (n=19) resulted in peripherally-migrated OPCs compared to control (n=5) at 72 hpf (FIG. 11A, p<0.01). We did not observe any morphological defects at this dose (FIG. 11C) so we used 1 ng/nl of adora2ab$^{MOI}$ for future experiments. Having identified an appropriate dose of MO, we then performed experiments to test whether adora2ab is required to prevent peripheral OPC migration. When we quantified peripherally-migrated OPCs in MO-injected animals, adora2ab$^{MOI}$ morphants (n=42), but not adora2aa$^{MOI}$ morphants (n=65), had significantly more peripheral OPCs at 3 dpf compared to uninjected (n=42) or phenol red-injected (n=11) embryos (p<0.0001) (FIG. 4B). This result is consistent with our finding that adora2aa$^{-/-}$ mutants do not have peripherally-migrated OPCs (FIG. 4A). We next injected adora2ab$^{MOI}$ into adora2aa$^{-/-}$ mutants expressing olig2: dsred and quantified the number of peripheral olig2$^+$ OPCs at 3 dpf. We observed peripheral OPCs only in mutants injected with adora2ab$^{MOI}$ (n=84) and not in uninjected (n=44) or phenol red-injected (n=30) mutants (FIG. 4C, p<0.0001). We conclude from these experiments that A2ab ARs are required to regulate OPC migration at the MEP TZ.

Figure 4D:
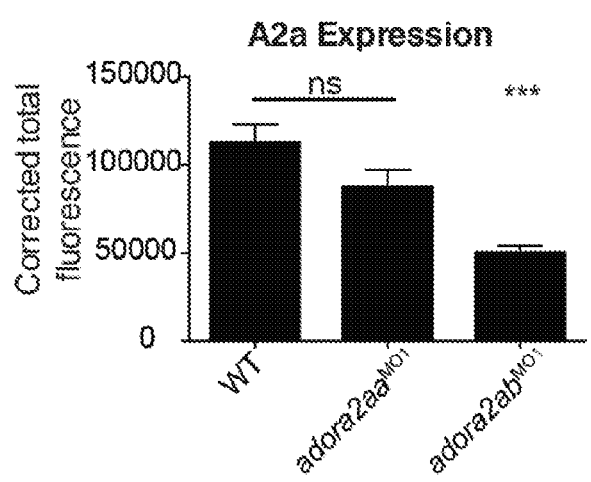

To validate that adora2ab$^{MOI}$ effectively knocked down A2ab AR protein expression, we injected olig2:dsred embryos with 1 ng/nl adora2aa$^{MOI}$ or adora2ab$^{MOI}$ and performed antibody labeling with an A2a antibody that has previously been used to detect expression in the zebrafish pancreas (Andersson et al., 2012). In preliminary experiments, we tested its specificity for A2ab vs A2aa ARs. We observed A2a antibody labeling in the spinal cord and along peripheral nerves at 50 hpf (FIG. 11B), which is consistent with previously described expression of adora2ab mRNA in the spinal cord (Boehmler et al., 2009). Embryos injected with 1 ng/nl adora2ab$^{MOI}$ (n=80) had significantly reduced A2ab AR expression along motor nerve roots at 50 hpf compared to WT (n=20 nerves) and adora2aa$^{MOI}$ injected embryos (n=59 nerves) (p<0.0001) (FIG. 4D and FIG. 11B).

Figures 4E, 4F, 4G:
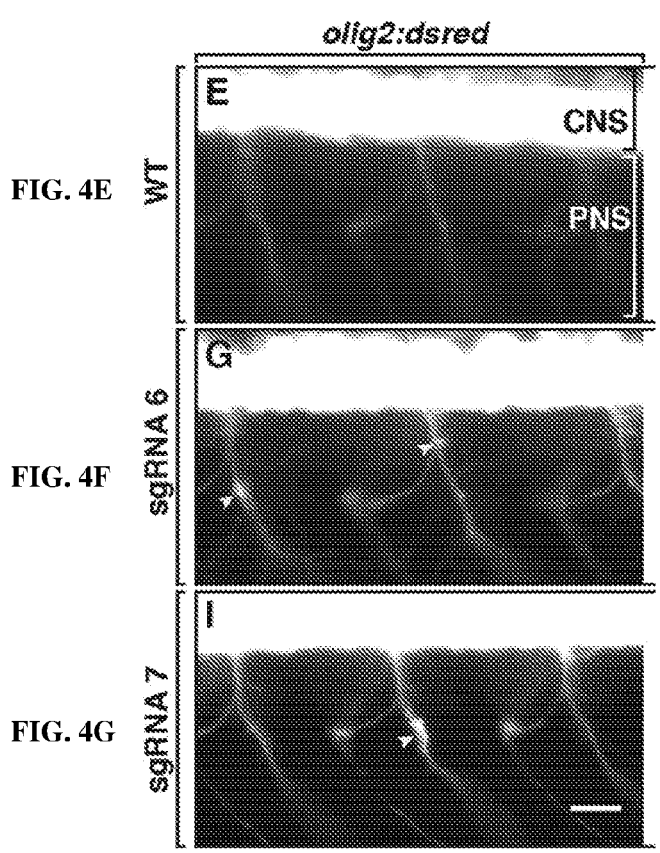

To confirm that our previous results were not due to off-target effects of the MO, we generated mutations in the adora2ab gene using CRISPR/Cas9. We designed 2 sgRNAs targeting adora2ab exon 2, just downstream of the translation start site, and injected the sgRNA along with Cas9 protein into olig2:egfp or olig2:dsred embryos at the 1 cell stage (FIG. 12). We confirmed that each sgRNA produced frameshift mutations in adora2ab by TOPO cloning and sequencing individual DNA clones from FO injected embryos (data not shown). Embryos injected with Cas9 and a previously published sgRNA targeting tyr or slc45a2, which both affect pigment formation and are not expected to affect OPC migration, were used as controls (Irion et al., 2014; Jao et al., 2013). We then quantified the number of larvae with peripherally-migrated olig2$^+$ OPCs at 3 dpf (Table 3). After analysis, DNA from individual embryos was sequenced to identify CRISPR-induced indels in adora2ab. FIGS. 4E, 4G, and 4I show representative WT and FO larvae injected with sgRNA6 or sgRNA7. Olig2$^+$ OPCs can be seen in the periphery of FO larvae, and the adora2ab sequences shown in 4F, G, and J correspond to the individual larvae in 4E, G and I. For gRNA 6, 24.7% (18/73) of injected larvae had peripheral olig2$^+$ OPCs. Of the larvae with peripheral OPCs, 100% (18/18) had frameshift mutations in adora2ab. For gRNA 7, 28% (23/82) of injected larvae had peripheral OPCs, and of the larvae with this phenotype, 95.7% (22/23) had frameshift mutations in adora2ab (Table 3).

We used previously published sgRNAs targeting tyr or slc45a2 to control for off-target effects of CRISPR injections. Out of 28 olig2:dsred larvae injected with either tyr or slc45a2 sgRNA, 26 (96.3%) had the expected pigmentation phenotype, whereas only 1 (3.6%), had peripheral olig2$^+$ OPCs. Additionally, injections of tyr or slc45a2 sgRNa did not result in any mutations in adora2ab.

Finally, we injected adora2ab sgRNA into adora2aa$^{-/-}$ embryos to determine if perturbation of adora2ab resulted in peripheral OPC migration. At 72 hpf, we observed peripheral OPCs in 5/14 (35.7%) adora2aa mutants. Of the larvae with peripheral OPCs, 100% (5/5) had mutations in adora2ab (Table 3). These results support our previous MO data and confirm that A2ab ARs are specifically required to prevent peripheral OPC migration.

Neuronal Activity Influences Peripheral OPC Migration

Figure 5A:
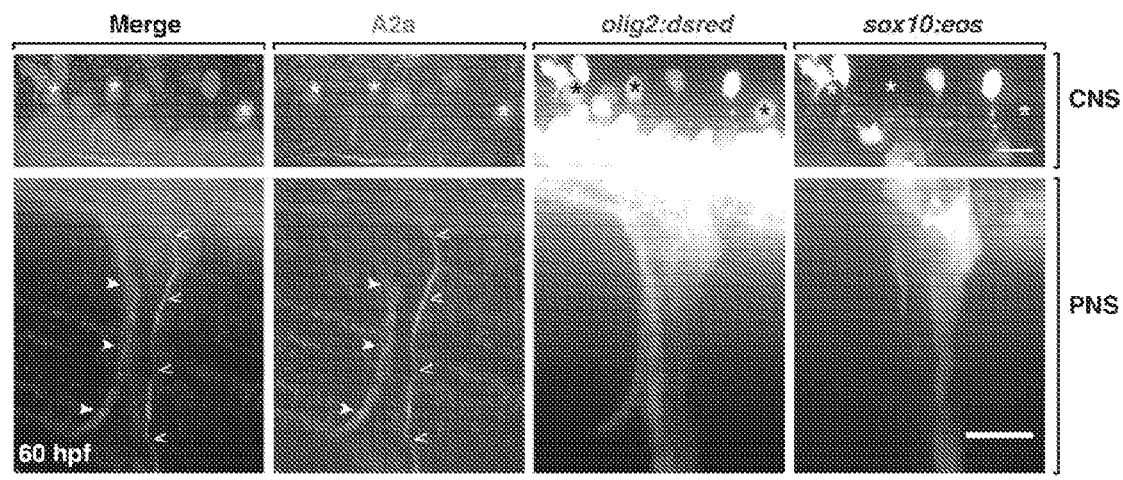
FIG. 5 comprises FIGS. 5A-5H. Modulation of neuronal activity affects OPC migration. (5A) Lateral views of 60 hpf WT olig2:dsred;sox10:eos larvae stained with A2a AR antibody. Upper panels show spinal cord (CNS) with A2a expression in a subset of olig2$^+$ motor neurons (asterisks) and axons. Lower panels (PNS) show peripheral spinal nerves with A2a expression in motor (closed arrowheads) and sensory (open arrowheads) axons. (5B) 72 hpf WT sox10:eos larvae stained with A2a antibody. A2a expression is present in peripheral motor (closed arrowheads) and sensory (open arrowheads) axons. (5C) Olig2:egfp embryo labeled with SCH-red fluorescent antagonist. Arrowheads mark spinal cord olig2$^+$ motor neurons. (5D) Mean±SEM peripheral OPCs per larvae at 3 dpf after treatment with carbenoxolone from 36 to 72 hpf. n=8 (0 µM), n=9 (1.25 µM), n=10 (2.5 µM), n=9 (5 µM), n=5 (10 µM), n=9 (20 µM) and n=1 (40 µM. 9 other larvae at this dose died. 40 µM dose was excluded from statistical analysis). * p<0.05 , p<0.001 compared to 0 µM. (5E) Mean±SEM of peripheral OPCs per larvae at 3 dpf following TeNT mRNA injections. n=66 (uninjected), n=44 (TeNT).  p=0.002. (5F) Mean±SEM of peripheral OPCs per larvae at 3 dpf after treatment from 36 to 72 hpf with 10 µM carbenoxolone with or without TeNT mRNA. TeNT+Carb n=10, Carb n=8, * p=0.04. (5G) Mean±SEM peripheral OPCs per larvae at 3 dpf after treatment with NBQX from 36 to 72 hpf n=22-25 larvae per dose. * p<0.05 ** p<0.001 compared to DMSO. (5H) Mean±SEM peripheral OPCs per larvae at 3 dpf after treatment with MK-801 from 36 to 72 hpf. n=31 (0 µM), n=11 (10 µM), n=20 (20 µM) and n=24 (40 µM), n=36 (80 µM). * p<0.05, ** p<0.001 compared to 0 µM. Scale bars, 20 µM.
Figure 5B:
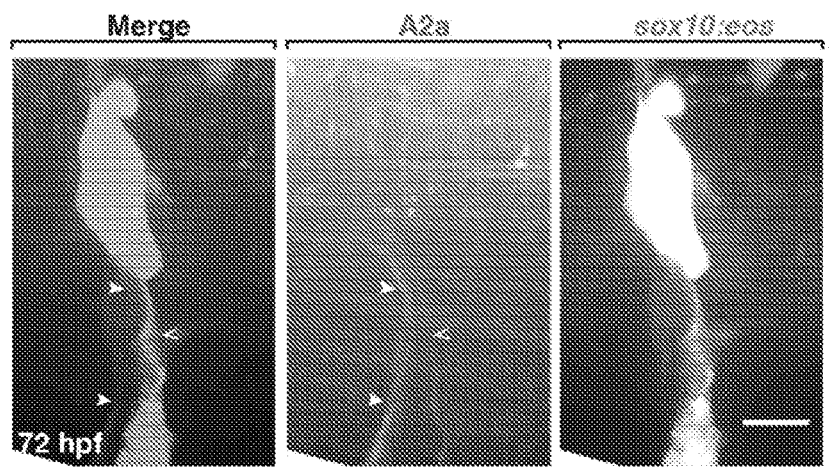
Figure 5C:
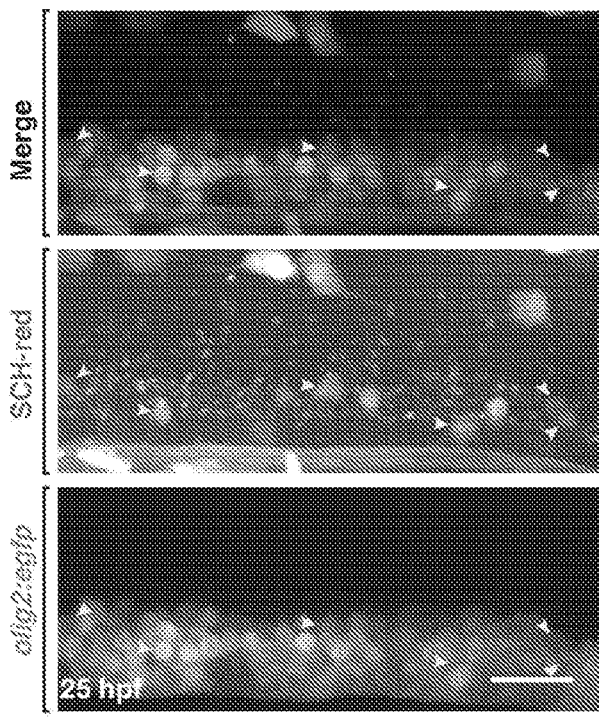
Figure 5D:
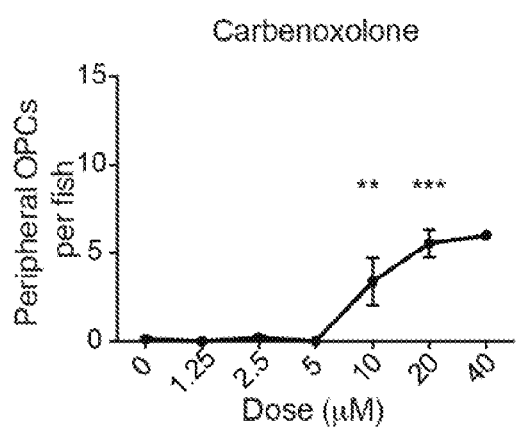
Figure 5E:
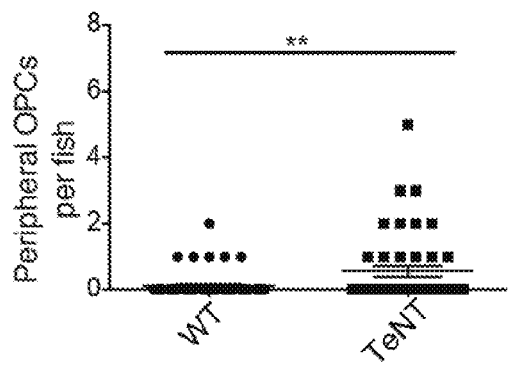
Figure 5F:
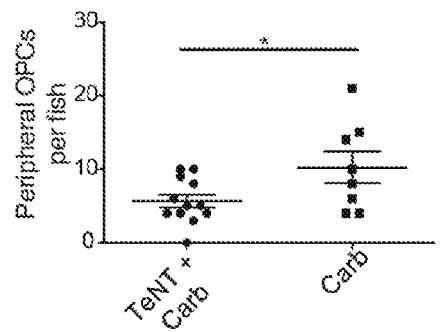

Adenosine signaling through A2a ARs is a well-known neuromodulatory pathway that generally acts to increase neurotransmitter release (Ciruela et al., 2006; Golder et al., 2008; Rebola et al., 2008). Adenosine has also been shown to affect migration of multiple cell types, including OPCs (Bao et al., 2013; Kronlage et al., 2010; Othman et al., 2003). To determine whether adenosine signaling through A2a ARs regulates peripheral OPC migration directly as a repulsive cue to OPCs, or indirectly by modifying neuronal activity, we assessed the expression of the A2a AR during developmental stages when we observed ectopic OPC migration across the MEP TZ We observed A2a antibody at 60 and 72 hpf, expression on peripheral motor and sensory axons, as well as on some neuronal cell bodies and axons in the spinal cord, including olig2$^+$ motor neurons (FIGS. 5A&B). We did not detect any A2a AR expression on OPCs or other glial cells at these stages. When we used fluorescently-tagged SCH-58261 (SCH-red), we observed SCH-red binding to olig2+ spinal cord motor neurons at 25 hpf (FIG. 5C). This expression pattern matches the previously published expression of adora2ab mRNA, and further supports the selectivity of SCH-58261 for zebrafish A2a ARs (Boehmler et al., 2009). Because A2a ARs are expressed by neurons in the spinal cord and nerve root axons and not OPCs, we hypothesized that adenosine signaling must modify OPC migration by altering neuronal activity. Because adenosine is a well-known modulator of neuronal activity, we decided to test whether neuronal activity itself could regulate OPC migration during development.

OPCs express many neurotransmitter receptors, and recent work demonstrates a role for neuronal activity in OL myelination (Bergles et al., 2000; Etxeberria et al., 2016; Gibson et al., 2014; Hines et al., 2015; Mensch et al., 2015; Stevens et al., 2002). Generally, adenosine binding to A2a ARs on neurons increases firing (Sebastiao and Ribeiro, 2015). Therefore, we hypothesized that inhibiting A2a ARs decreased neuronal activity, which resulted in peripheral OPC migration. To test this hypothesis, we used two independent approaches. First, early in development, many zebrafish neurons are electrically coupled by gap junctions (Saint-Amant and Drapeau, 2001). Therefore, we treated olig2:dsred zebrafish larvae from 36 to 72 hpf with the gap junction blocker, carbenoxolone, in order to inhibit these electrically coupled neurons. Consistent with our hypothesis, blocking gap junctions resulted in significant numbers of peripherally-migrated OPCs (FIG. 5D, p<0.001 for 10 μM carbenoxolone and p<0.0001 for 20 μM carbenoxolone n=5 to 10 larvae per dose). Second, we inhibited all synaptic vesicle release by expressing tetanus toxin light chain (TeNT) (Yu et al., 2004). Previous studies demonstrate that injections of TeNT mRNA effectively inhibit synaptic vesicle release and result in significant paralysis of zebrafish larvae at 3 and 4 dpf (Fontenas et al., 2016; Mensch et al., 2015). When we injected olig2:dsred embryos at the 1 to 2 cell stage with 1-2 nl of 175 ng/μl TeNT mRNA, we confirmed that neuronal activity was indeed inhibited by confirming that larvae were paralyzed at 2 (n=54) and 3 dpf (n=52) (FIG. 13, 2 dpf p<0.0001; 3 dpf p<0.0001). Consistent with our hypothesis, silencing neurons using TeNT resulted in the peripheral migration of significant numbers of OPCs compared to controls (FIG. 5E p=0.002, TeNT 0.5682±0.1639 (mean±SEM), n=44; WT 0.1077±0.04452 (mean±SEM), n=65).

Because zebrafish have a combination of electrically and chemically coupled neurons at the developmental stages we were assaying, inhibiting one or the other may silence different populations of neurons (Saint-Amant and Drapeau, 2001). We therefore combined TeNT and carbenoxolone treatments to investigate if a more complete silencing of neuronal activity would result in greater numbers of peripheral OPCs than either treatment alone. To perform this experiment, we injected olig2:dsred embryos at the 1 to 2 cell stage with TeNT mRNA and then treated them from 36 to 72 hpf with 10 μM carbenoxolone. At 72 hpf, we quantified peripheral OPCs and compared them to larvae treated with 10 μM carbenoxolone only. Intriguingly, carbenoxolone treatment alone resulted in more peripherally-migrated OPCs than carbenoxolone combined with TeNT (FIG. 5F; p=0.04; carb n=8; TeNT+carb n=12). We conclude from these experiments that neuronal activity is involved in restricting OPC migration at the MEP TZ, and that adenosine is necessary to regulate this neuronal activity.

Figure 5G:
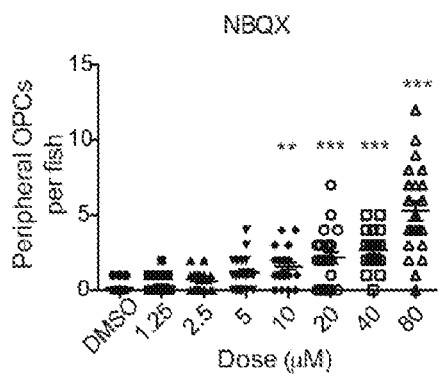
Figure 5H:
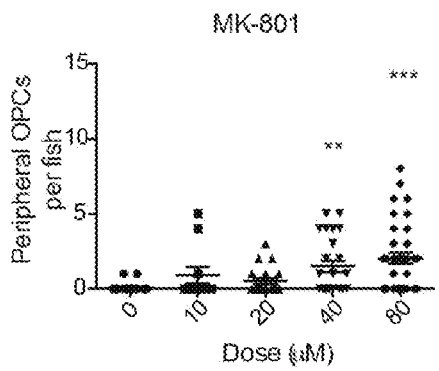

Recent work demonstrates that activity-dependent vesicular release from neurons can influence OPC differentiation and/or myelination (Bergles et al., 2000; 2010; Hines et al., 2015; Koudelka et al., 2016; Mensch et al., 2015). Therefore, we hypothesized that neuronal activity might act to regulate OPC migration at the MEP by releasing neurotransmitters that influence OPCs. In support of this, studies demonstrate that OPCs express functional neurotransmitter receptors that become activated in response to neuronal firing (Bergles et al., 2000; Lin and Bergles, 2004b). Therefore, we sought to identify the neuronal signal that might regulate OPC migration at the MEP by inhibiting neurotransmitter receptors. To do this, we treated olig2:dsred larvae from 36 to 72 hpf with neurotransmitter receptor antagonists and quantified the number of peripherally migrated OPCs at 3 dpf. The selective AMPAR antagonist, NBQX, resulted in significant numbers of peripherally-migrated OPCs compared to control (FIG. 5G). Similarly, treatment with the NMDAR antagonist, MK-801, also resulted in peripheral OPC migration (FIG. 5H). These results are consistent with the hypothesis that neuronally-released glutamate may regulate OPC migration at the MEP. However, we are unable to selectively inhibit OPC AMPA or NMDA receptors, so we cannot rule out the possibility that neuronal NMDA and/or AMPA receptors may also be involved.

Peripherally-Migrated OPCs Rescue Myelin Deficits in a Peripheral Neuropathy Model Our data demonstrates that A2ab AR inhibition results in OPC migration onto peripheral spinal motor nerves without otherwise disturbing overall nerve development. This led us to hypothesize that OPCs could be pharmacologically recruited onto peripheral nerves in order to myelinate them. Previous studies from the lab demonstrate that peripheral OPCs are capable of initiating myelination of peripheral nerves (Kucenas et al., 2009; Morris et al., 2017; Smith et al., 2014). However, in these studies, OPCs populated the nerve in the context of genetic mutations resulting in the death or absence of both SCs and MEP glia. Therefore, we wanted to determine if it was possible to recruit OPCs to myelinate peripheral motor nerves in a model more closely resembling human peripheral neuropathies, in which SCs are present, but fail to myelinate. To do this, we used zebrafish harboring a mutation in g protein coupled receptor 126 (gpr126), a model of peripheral neuropathy in which SCs ensheath, but fail to myelinate peripheral nerves (Monk et al., 2009). OLs are present in normal numbers in these mutants, and central myelination is completely normal (Monk et al., 2009).

We first tested whether untreated gpr126 mutants had functional MEP glia. As we previously described, MEP glia along the spinal motor root can be identified by expression of the specific marker wif1 at 72 hpf, or by fate mapping with photoconversion of the sox10:eos transgenic line (Smith et al., 2014). The nascent Eos protein exists in a green fluorescent state, but when exposed to UV light, it permanently shifts to a red fluorescent state. When we exposed whole embryos to UV light at 48 hpf, all neural crest-derived cells were photoconverted to red fluorescence. MEP glia, which are not neural crest-derived and begin expressing sox10:eos after 48 hpf, are not photoconverted and can be identified as green fluorescent cells on the nerve root by 54 hpf (Smith et al., 2014). Using both wif1 and photoconverted sox10:eos as tools to visualize MEP glia, we found that these cells were present on spinal motor roots in gpr126 mutants at 72 hpf (FIGS. 6A&B). When we quantified peripheral OPC migration in olig2:dsred;gpr126 mutants at 3 dpf, we did not observe any peripheral OPCs in mutants treated with DMSO (FIG. 6C, n=8). These data demonstrate that MEP glia are present and functioning properly and that the absence of myelin on peripheral nerves is not sufficient to elicit peripheral OPC migration.

Therefore, we tested whether treatment with the A2a AR antagonist would result in peripherally-migrated OPCs ensheathing peripheral spinal motor nerves in these mutants. When we treated gpr126 mutants with 10 μM of the A2a AR antagonist SCH-58261 from 36 to 72 hpf, we observed a significant number of olig2$^+$ OPCs in the periphery compared to DMSO-treated controls (FIG. 6C, p=0.009, n=6). We then performed in vivo, time-lapse imaging on nkx2.2a: megfp;olig2:dsred;gpr126$^{-/-}$ mutants in order to visualize whether these peripheral OPCs initiated myelination of peripheral nerves. The transgene nkx2.2a:megfp is expressed by pre-myelinating OPCs and enables clear visualization of membrane structures (Kucenas et al., 2008a). No other cells in the spinal cord or at the MEP TZ express both nkx2.2a and olig2, so use of these transgenes allowed us to unambiguously identify membrane sheaths coming from OPCs. We performed in vivo, time-lapse imaging on larvae treated with SCH-58261 from 36 to 72 hpf and observed nkx2.2a$^+$/olig2$^+$ OPCs initiate ensheathment of peripheral spinal motor axons. Thin OPC membrane processes extended toward peripheral motor axons and formed membrane sheaths around them (FIG. 6D). The timing of sheath initiation on peripheral axons coincided with sheath initiation within the spinal cord, and some peripheral sheaths stabilized and elongated during the course of the time-lapse (FIG. 6D). This time-lapse data rules out the possibility that SCH-58261 treatment stimulates SCs to myelinate the nerve, since nkx2.2a$^+$ OPC processes can be clearly seen ensheathing nerve segments.

Figure 6E:
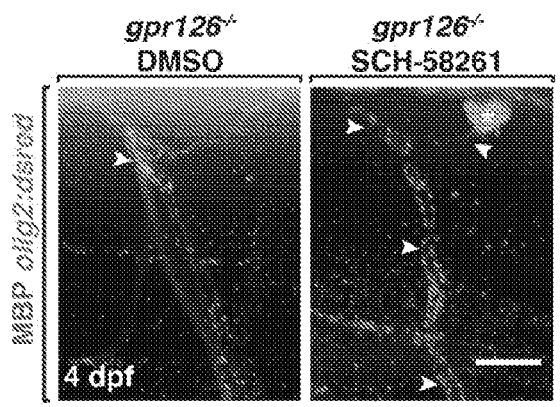
FIG. 6 comprises FIGS. 6A-6F. Peripheral OPCs myelinate spinal motor axons in a peripheral neuropathy model. (A) In situ hybridization for wif1 in WT and gpr126$^{-/-}$ larvae at 72 hpf shows MEP glia (arrowheads). SC, spinal cord; N, notochord. (B) Live images of photoconverted sox10:eos larvae at 72 hpf show unconverted (green) Eos$^+$ MEP glia (arrowheads) in both WT and gpr126$^{-/-}$ larvae. (C) Mean±SEM of peripheral OPCs in 72 hpf gpr126$^{-/-}$ larvae treated with DMSO or SCH-58261 from 36 to 72 hpf n=8 (DMSO), n=6 (SCH-58261). ** p=0.009. (D) Frames from a 15 hour time-lapse movie of a olig2:dsred;nkx2.2a:megfp.
Figure 6F:
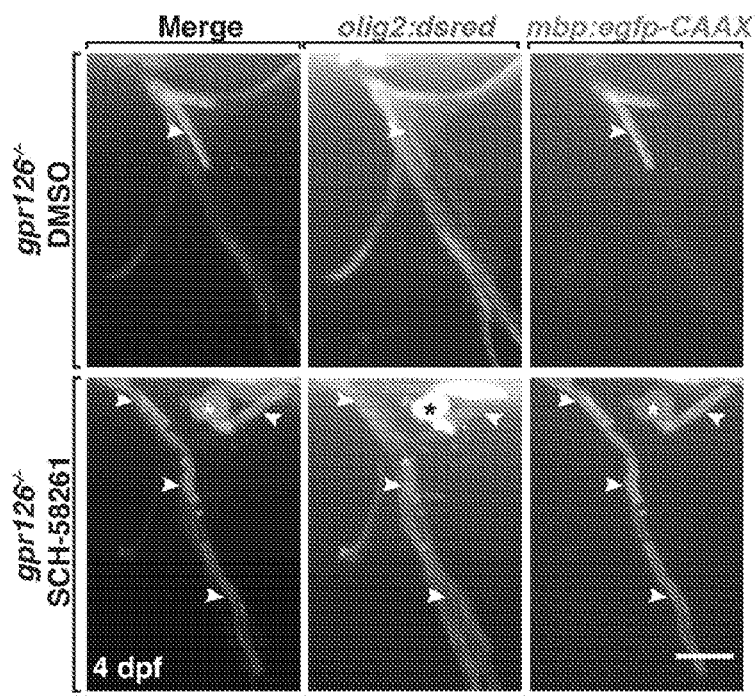

To examine whether these membrane sheaths were in fact myelin, we treated gpr126 mutants from 36 to 72 hpf with SCH-58261 or DMSO, fixed larvae at 4 dpf, and labeled with an antibody specific to myelin basic protein (MBP) using immunohistochemistry (Kucenas et al., 2009). In mutants treated with DMSO, we observed MBP only on a short segment of the proximal nerve root (FIG. 6E), which is consistent with our previous data showing that differentiated MEP glia express MBP in this region (Smith et al., 2014). In mutants treated with the A2a AR antagonist, MBP labeling was present further distally along the nerve (FIG. 6E). As further confirmation that peripheral OPCs myelinate spinal motor nerve roots following treatment with SCH-58261, we imaged gpr126$^{-/-}$ larvae expressing the transgenes mbp:egfp and olig2:dsred from 72 to 86 hpf (n=3) (FIG. 6F). In these time-lapses, we observed olig2$^+$ OPCs beginning to ensheath peripheral nerves with mbp$^+$ membrane tubes. Out of 12 nerves imaged, OPCs migrated out of the spinal cord onto 4 nerves, and an additional 3 nerves had OPCs already present at the beginning of the time-lapse. Multiple EGFP$^+$ membrane tubes extended from single OPCs and ensheathed most of the nerve root on all 7 nerves with OPCs present. These long membrane tubes were consistent with the pattern of MBP antibody labeling on the nerves of SCH-58261-treated mutants (FIG. 6E). Both the MBP antibody and mbp:egfp labeling were closely associated with an olig2$^+$ cell body, providing further evidence that peripherally-migrated OPCs and not SCs, initiate myelination in gpr126 mutants treated with SCH-58261 (FIGS. 6D&E). From these experiments, we conclude that OPCs can be recruited onto peripheral motor nerves and initiate myelination, even in the presence of MEP glia and SCs.

Discussion

At MEP TZs, motor axons originating within the spinal cord cross through the glia limitans and transition into the PNS (Bonanomi and Pfaff, 2010). OPCs, in contrast, originate within the CNS but do not cross into the periphery, despite being highly migratory and extending membrane processes into the TZ (Fraher and Kaar, 1984; Smith et al., 2014). The mechanisms responsible for allowing axons and other glial populations to cross through the MEP TZ while preventing peripheral OPC migration are not fully understood, although work from our lab and others demonstrates that MEP glia in zebrafish and BC cells in mice are necessary to restrict OPC migration (Coulpier et al., 2010; Fröb et al., 2012; Smith et al., 2014). Using selective inhibitors for AR subtypes combined with genetic manipulation, we show that the A2ab AR is essential for preventing peripheral migration of OPCs, identifying adenosine signaling as a novel regulator of glial segregation at MEP TZs. We also provide evidence that neuronal A2a AR signaling is selectively required to prevent OPCs from migrating into the PNS during development.

Adenosine and Activity-Dependent Regulation of OPCs

Interestingly, in our experiments, adenosine does not act directly on OPCs. Rather, neurons in the spinal cord and spinal nerve root axons express A2ab ARs, and antagonizing neuronal A2ab ARs results in peripheral OPC migration. Previous studies demonstrate that neuronal A2ab ARs facilitate neuronal firing (Sebastiao and Ribeiro, 2015). Since neuronal A2a AR activation generally increases neurotransmitter release, in our experiments, antagonizing A2a AR would likely decrease neuronal activity. Additionally, changes in neuronal activity are detected by OPCs and affect their differentiation (Lin and Bergles, 2004a). This supports a model in which A2a AR regulation of neuronal activity is necessary to prevent peripheral migration of OPCs (FIG. 7). Our finding that inhibiting neuronal firing with TeNT or carbenoxolone also results in peripheral OPC migration further supports this model. This is consistent with studies showing that decreased neuronal activity altered OPC distribution in mouse brains (Mangin et al., 2012; Tong et al., 2009). The results presented here link two fields of study: neuromodulation by adenosine and activity-dependent regulation of OPCs. Our screen not only discovered adenosine signaling as a regulator of OPC repulsion at the MEP, but also 5 other compounds related to neuronal activity: 1-Phenyl-3-(2-thiazolyl)-2-thiourea and Brefeldin A, which interfere with the production and secretion of neurotransmitters; acetylthiocholine chloride and Salmetrol xinfoate, neurotransmitter receptor antagonists; and N-Phenylanthranilic acid, a chloride channel blocker which would disrupt membrane potentials. Further studies are needed to characterize the mechanisms driving ectopic OPC migration in zebrafish treated with these neuromodulators.

Taken together, these experiments strengthen growing evidence from multiple labs that neuronal activity regulates OPC and OL behaviors (Gallo et al., 2008). Studies in mice and zebrafish demonstrate that increased neuronal activity promotes OPC differentiation and myelination, whereas decreased activity inhibits differentiation and leads to hypomyelination (Gibson et al., 2014; Hines et al., 2015; Makinodan et al., 2012; Mensch et al., 2015; Stevens et al., 2002). We hypothesize that because neuronal activity leads to OPC differentiation, decreased activity in our experiments would result in OPCs failing to differentiate, which would cause them to maintain their highly migratory, exploratory behavior. Because MEP glia are involved in repelling peripheral OPC migration, we considered the possibility that A2ab-dependent neuronal activity could affect MEP glia differentiation. However, in our experiments, MEP glia have normal morphology and express both wif1 and MBP, demonstrating normal differentiation. Therefore, our data supports the hypothesis that the effects of adenosine and neuronal activity directly affect OPCs.

Glutamate and OPC Migration

We have also sought to identify what signal is released by neurons to affect OPC repulsion at the MEP TZ. Glutamate, GABA, and acetylcholine are all likely candidates, as OPCs express receptors for each of these neurotransmitters (Lin and Bergles, 2004a). Synapses between OPCs and neurons have been observed using electron microscopy, and vesicular release of glutamate from neurons activates AMPA and/or NMDA receptors on OPCs (Bergles et al., 2000). We observed that AMPAR and NMDAR antagonists resulted in increased ectopic migration of OPCs through MEP TZs, suggesting that glutamate is important in regulating OPC migration. This is consistent with in vitro studies showing that glutamate affects OPC migration (Gudz et al., 2006; Xiao et al., 2013). We also note the possibility that OPCs could respond to other factors released from neurons in an activity-dependent manner, such as ATP (Fields and Stevens, 2000). A recent study in zebrafish demonstrated that myelination can be modified by neuronal activity from certain classes of neurons, but is unresponsive to changes in activity of others (Koudelka et al., 2016). It would be interesting to know whether this is because of the particular neurotransmitters released by different neuronal populations, and if the same populations of neurons regulate OPC migration. This could also explain our surprising result that inhibiting all neuronal activity with TeNT did not result in as many peripheral OPCs compared to inhibiting subsets of neurons with A2a antagonists or carbenoxolone. In a review of synaptic communication between neurons and OPCs, Gallo et al. proposed that an OPC could detect relative differences in activity among populations of neurons, and this hypothesis has been supported experimentally (Etxeberria et al., 2016; Gallo et al., 2008; Hines et al., 2015). If OPCs detect differences in activity among neuronal populations, inhibiting all neuronal firing would not be expected to have as strong an effect on OPC migration. It is likely that many overlapping mechanisms regulate spinal cord OPC migration, since most OPCs remain in the spinal cord in our experiments. We have not yet explored whether OPCs could be following signals other than glutamate, or whether endogenous neuromodulators other than adenosine also play a role in regulating their release.

Potential for Peripheral OPCs to Myelinate Peripheral Nerves

Our findings also offer intriguing possibilities for the treatment of peripheral neuropathies. We and others have shown that OPCs are capable of myelinating peripheral axons (Coulpier et al., 2010; Kucenas et al., 2009; Morris et al., 2017; Smith et al., 2014). However, these previous studies were in the context of genetic mutations that result in the loss of all peripheral myelinating glia. In our model, SCs are present on nerves, but they fail to make myelin, which is a feature of some forms of Charcot-Marie-Tooth disease. Our data as well as previous studies in mice and zebrafish demonstrate no peripheral OPC migration in mutants with peripheral hypomyelination, and it is unclear whether OPCs would naturally migrate onto peripheral nerves in human neuropathy patients (Coulpier et al., 2010; Monk et al., 2009). Because of this, we are excited by the possibility of inducing OPCs to migrate onto peripheral nerves that lack myelin. Once in the periphery, OPCs are competent to initiate myelination without continued drug treatment. In combination with previous studies, this is strong evidence for the potential for OPCs to myelinate peripheral nerves in disease.

TABLE 1

Validated hits from screen using LOPAC ®$^{1280}$.

| Drug name | Description |
| --- | --- |
| CGS-15943 | Highly potent, non selective adenosine receptor antagonist |
| 1-Phenyl-3-(thiazolyl)-2-thiourea | Dopamine β-hydroxylase inhibitor |
| Acetylthiocholine chloride | Nicotinic acetylcholine receptor agonist |
| Brefeldin A from *Penicillium brefeldianum* | Causes collapse of Golgi apparatus, blocking exocytosis |
| N-Phenylanthranilic acid | Cl-channel blocker |
| Salmeterol xinafoate | Selective β2 adrenergic receptor agonist |
| I-OMe-Tyrphostin AG 538 | Insulin growth factor I (IGF-1) receptor inhibitor |
| L-Canavanine sulfate | Selective inhibitor of inducible nitric oxide synthase (iNOS) |
| Clofibrate | Peroxisome proliferator-activated receptor-α (PPARα) agonist |
| Wortmannin from *Penicillium funiculosum* | Selective phosphatidylinositol 3-kinase (PI3-K) inhibitor |

The first six chemicals of Table 1 are predicted to affect neuronal activity. The others can be used to stimulate OPC migration via different mechanisms than by regulating neuronal activity.

SUPPLEMENTAL TABLE 1

Transgenes used in this study, with abbreviations and descriptions of structures labeled.

| Transgene name | Abbreviation | Description |
| --- | --- | --- |
| Tg(sox10(4.9):eos) | Sox10:eos | Photoconvertible (green to red) Eos protein expressed by OPCs, Schwann cells, MEP glia and some interneurons |
| Tg(olig2:egfp)$^{vu12}$ | olig2:egfp | GFP expressed by motor neurons and axons, OPCs, MEP glia and some interneurons |
| Tg(olig2:dsred)$^{vu19}$ | olig2:dsred | DsRed expressed by motor neurons and axons, OPCs, MEP glia and some interneurons |
| Tg(nkx2.2a:megfp)$^{vu17}$ | nkx2.2a:megfp | Membrane-tethered GFP expressed by perineurial glia and myelinating OPCs |
| Tg(mbp:egfp-CAAX) | mbp:megfp | Membrane-tethered GFP expressed by myelinating glia |

SUPPLEMENTAL TABLE 2

| CRISPR sgRNA efficiency. | | |
| --- | --- | --- |
| | Mutation efficiency (%) | Total injected |
| adora2ab sgRNA 6 | 11 (91.7%) | 12 |
| adora2ab sgRNA 7 | 13 (86.7%) | 15 |
| scl45a2 sgRNA | 34 (94.4%) | 36 |
| tyr sgRNA | 29 (87.9%) | 33 |

Individual injected larvae were randomly chosen for sequencing and detection of mutations in the target gene to determine sgRNA efficiency. Control sgRNA efficiency was quantified as the number of injected larvae with defects in pigment formation.

SUPPLEMENTAL TABLE 3

F0 CRISPR injection data. For number of larvae with peripheral OPCs, percent of total injected larvae is given. Each larvae with peripheral OPCs was sequenced to detect mutations in adora2ab, and the percentage of the number with peripheral OPC phenotype is given. For slc45a2 and tyr sgRNA, 12 larvae were randomly selected for adora2ab sequencing, and the percentage of those samples with mutations in adora2ab is given.

| | Total number injected | Number with ectopic OPCs (%) | Number with ectopic OPCs and mutation (%) | Number with ectopic OPCs but no mutation (%) |
| --- | --- | --- | --- | --- |
| adora2ab sgRNA 6 | 73 | 18 (24.7%) | 18 (100%) | 0 (0%) |
| adora2ab sgRNA 7 | 82 | 23 (28.0%) | 22 (95.7%) | 1 (4.3%) |
| adora2aa$^{-/-}$ adora2ab sgRNA | 14 | 5 (35.7%) | 5 (100%) | 0 (0%) |
| control sgRNA | 28 | 1 (3.6%) | Number with adora2ab mutation 0 (0%) | |

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

Abbracchio, M., Burnstock, G., Verkhratsky, A., and Zimmermann, H. (2009). Purinergic signalling in the nervous system: an overview. Trends in Neurosciences 32, 19-29.

Almeida, R. G., Czopka, T., Ffrench-Constant, C., and Lyons, D. A. (2011). Individual axons regulate the myelinating potential of single oligodendrocytes in vivo. Development 138, 4443-4450.

Andersson, O., Adams, B. A., Yoo, D., Ellis, G. C., Gut, P., Anderson, R. M., German, M. S., and Stainier, D. Y. (2012). Adenosine signaling promotes regeneration of pancreatic β cells in vivo. Cell Metab. 15, 885-894.

Bao, Y., Chen, Y., Ledderose, C., Li, L., and Junger, W. G. (2013). Pannexin 1 channels link chemoattractant receptor signaling to local excitation and global inhibition responses at the front and back of polarized neutrophils. J Biol Chem 288, 22650-22657.

Bergles, D. E., and Richardson, W. D. (2015). Oligodendrocyte Development and Plasticity. Cold Spring Harb Perspect Biol 8, a020453.

Bergles, D. E., Roberts, J. D., Somogyi, P., and Jahr, C. E. (2000). Glutamatergic synapses on oligodendrocyte precursor cells in the hippocampus. Nature 405, 187-191.

Binari, L. A., Lewis, G. M., and Kucenas, S. (2013). Perineurial glia require Notch signaling during motor nerve development but not regeneration. J Neurosci 33, 4241-4252.

Boch, J., Scholze, H., Schornack, S., Landgraf, A., Hahn, S., Kay, S., Lahaye, T., Nickstadt, A., and Bonas, U. (2009). Breaking the code of DNA binding specificity of TAL-type III effectors. Science 326, 1509-1512.

Boehmler, W., Petko, J., Woll, M., Frey, C., Thisse, B., Thisse, C., Canfield, V. A., and Levenson, R. (2009). Identification of zebrafish A2 adenosine receptors and expression in developing embryos. Gene Expr Patterns 9, 144-151.

Bonanomi, D., and Pfaff, S. L. (2010). Motor Axon Pathfinding. Cold Spring Harb Perspect Biol 2, a001735.

Chen, J. F., Huang, Z., Ma, J., Zhu, J., Moratalla, R., Standaert, D., Moskowitz, M. A., Fink, J. S., and Schwarzschild, M. A. (1999). A(2A) adenosine receptor deficiency attenuates brain injury induced by transient focal ischemia in mice. J Neurosci 19, 9192-9200.

Chen, S., Oikonomou, G., Chiu, C., Niles, B., Liu, J., Lee, D., Antoshechkin, I., and Prober, D. (2013). A large-scale in vivo analysis reveals that TALENs are significantly more mutagenic than ZFNs generated using context-dependent assembly. Nucleic Acids Res.

Ciruela, F., Casadó, V., Rodrigues, R. J., Lujin, R., Burgueno, J., Canals, M., Borycz, J., Rebola, N., Goldberg, S. R., Mallol, J., et al. (2006). Presynaptic control of striatal glutamatergic neurotransmission by adenosine A1-A2A receptor heteromers. J. Neurosci. 26, 2080-2087.

Coulpier, F., Decker, L., Funalot, B., Vallat, J.-M., Garcia-Bragado, F., Charnay, P., and Topilko, P. (2010). CNS/PNS Boundary Transgression by Central Glia in the Absence of Schwann Cells or Krox20/Egr2 Function. J Neurosci 30, 5958-5967.

Dennis, J., Morgan, M., Graf, M., and Fuss, B. (2012). P2Y12 receptor expression is a critical determinant of functional responsiveness to ATX's MORFO domain. Purinergic Signal 8, 181-190.

Emery, B., and Lu, R. Q. (2015). Transcriptional and epigenetic regulation of oligodendrocyte development and myelination in the central nervous system. Cold Spring Harb Perspect Biol 7, a020461.

Etxeberria, A., Hokanson, K. C., Dao, D. Q., Mayoral, S. R., Mei, F., Redmond, S. A., Ullian, E. M., and Chan, J. R. (2016). Dynamic Modulation of Myelination in Response to Visual Stimuli Alters Optic Nerve Conduction Velocity. J Neurosci 36, 6937-6948.

Fields, R. D., and Stevens, B. (2000). ATP: an extracellular signaling molecule between neurons and glia. Trends Neurosci 23, 625-633.

Fontenas, L., Santis, F., Donato, V., Degerny, C., Chambraud, B., Bene, F., and Tawk, M. (2016). Neuronal Ndrg4 Is Essential for Nodes of Ranvier Organization in Zebrafish. PLOS Genet 12, e1006459.

Fraher, J. P., and Kaar, G. F. (1984). The transitional node of Ranvier at the junction of the central and peripheral nervous systems: an ultrastructural study of its development and mature form. J. Anat. 139 (Pt 2), 215-238.

Fröb, F., Bremer, M., Finzsch, M., Kichko, T., Reeh, P., Tamm, E., Charnay, P., and Wegner, M. (2012). Establishment of myelinating schwann cells and barrier integrity between central and peripheral nervous systems depend on Sox10. Glia 60, 806-819.

Gagnon, J. A., Valen, E., Thyme, S. B., Huang, P., Akhmetova, L., Ahkmetova, L., Pauli, A., Montague, T. G., Zimmerman, S., Richter, C., et al. (2014). Efficient mutagenesis by Cas9 protein-mediated oligonucleotide insertion and large-scale assessment of single-guide RNAs. PloS One 9, e98186.

Gallo, V., Mangin, J.-M. M., Kukley, M., and Dietrich, D. (2008). Synapses on NG2-expressing progenitors in the brain: multiple functions? J Physiol 586, 3767-3781.

Gibson, E., Purger, D., Mount, C., Goldstein, A., Lin, G., Wood, L., Inema, I., Miller, S., Bieri, G., Zuchero, J. B., et al. (2014). Neuronal Activity Promotes Oligodendrogenesis and Adaptive Myelination in the Mammalian Brain. Science 344, 1252304.

Golder, F., Ranganathan, L., Satriotomo, I., Hoffman, M., Lovett-Barr, M., Watters, J., Baker-Herman, T., and Mitchell, G. (2008). Spinal Adenosine A2a Receptor Activation Elicits Long-Lasting Phrenic Motor Facilitation. J Neurosci 28, 2033-2042.

Goujon, M., McWilliam, H., Li, W., Valentin, F., Squizzato, S., Paren, J., and Lopez, R. (2010). A new bioinformatics analysis tools framework at EMBL-EBI. Nucleic Acids Res 38, W695-W699.

Gudz, T. I., Komuro, H., and Macklin, W. B. (2006). Glutamate stimulates oligodendrocyte progenitor migration mediated via an alphav integrin/myelin proteolipid protein complex. J Neurosci 26, 2458-2466.

Haas, J., Frese, K. S., Park, Y. J., Keller, A., Vogel, B., Lindroth, A. M., Weichenhan, D., Franke, J., Fischer, S., Bauer, A., et al. (2013). Alterations in cardiac DNA methylation in human dilated cardiomyopathy. EMBO Mol Med 5, 413-429.

Hines, J. H., Ravanelli, A. M., Schwindt, R., Scott, E. K., and Appel, B. (2015). Neuronal activity biases axon selection for myelination in vivo. Nat Neurosci 18, 683-689.

Irion, U., Krauss, J., and Nüsslein-Volhard, C. (2014). Precise and efficient genome editing in zebrafish using the CRISPR/Cas9 system. Development 141, 4827-4830.

Jao, L.-E. E., Wente, S. R., and Chen, W. (2013). Efficient multiplex biallelic zebrafish genome editing using a CRISPR nuclease system. Proc. Natl. Acad. Sci. U.S.A. 110, 13904-9.

Jarvis, M., and Williams, M. (1989). Direct autoradiographic localization of adenosine A2 receptors in the rat brain using the A2-selective agonist, [3H] CGS 21680. Eur J Pharmacol 168, 243-246.

Jiang, J. L., van Rhee, A. M., Melman, N., Ji, X. D., and Jacobson, K. A. (1996). 6-phenyl-1,4-dihydropyridine derivatives as potent and selective A3 adenosine receptor antagonists. J. Med. Chem. 39, 4667-4675.

Keuerleber, S., Gsandtner, I., and Freissmuth, M. (2010). From cradle to twilight: The carboxyl terminus directs the fate of the A2A-adenosine receptor. Biochimica et Biophysica Acta (BBA)—Biomembranes 1808.

Kimmel, C. B., Ballard, W. W., Kimmel, S. R., Ullmann, B., and Schilling, T. F. (1995). Stages of embryonic development of the zebrafish. Dev. Dyn. 203, 253-310.

Kirby, B., N, Latimer, A., Shin, J., Carney, T., Kelsh, R., and Appel, B. (2006). In vivo time-lapse imaging shows dynamic oligodendrocyte progenitor behavior during zebrafish development. Nat. Neurosci. 9.

Koudelka, S., Voas, M. G., Almeida, R. G., Baraban, M., Soetaert, J., Meyer, M. P., Talbot, W. S., and Lyons, D. A. (2016). Individual Neuronal Subtypes Exhibit Diversity in CNS Myelination Mediated by Synaptic Vesicle Release. Curr Biol 26, 1447-1455.

Kronlage, M., Song, J., Sorokin, L., Isfort, K., Schwerdtle, T., Leipziger, J., Robaye, B., Conley, P. B., Kim, H.-C. C., Sargin, S., et al. (2010). Autocrine purinergic receptor signaling is essential for macrophage chemotaxis. Sci Signal 3, ra55.

Kucenas, S., Snell, H., and Appel, B. (2008a). nkx2.2a promotes specification and differentiation of a myelinating subset of oligodendrocyte lineage cells in zebrafish. Neuron Glia Biol 4, 71-81.

Kucenas, S., Takada, N., Park, H.-C. C., Woodruff, E., Broadie, K., and Appel, B. (2008b). CNS-derived glia ensheath peripheral nerves and mediate motor root development. Nat. Neurosci. 11, 143-151.

Kucenas, S., Wang, W., Knapik, E., and Appel, B. (2009). A selective glial barrier at motor axon exit points prevents oligodendrocyte migration from the spinal cord. J Neurosci 29, 15187-15194.

De Lera Ruiz, M., Lim, Y.-H. H., and Zheng, J. (2014). Adenosine A2A receptor as a drug discovery target. J Med Chem 57, 3623-3650.

Lewis, K. E., and Eisen, J. S. (2003). From cells to circuits: development of the zebrafish spinal cord. Prog. Neurobiol. 69, 419-449.

Lin, S.-C. C., and Bergles, D. E. (2004a). Synaptic signaling between neurons and glia. Glia 47, 290-298.

Lin, S. C., and Bergles, D. E. (2004b). Synaptic signaling between GABAergic interneurons and oligodendrocyte precursor cells in the hippocampus. Nat Neurosci 7, 24-32.

Lyons, D. A., Pogoda, H.-M. M., Voas, M. G., Woods, I. G., Diamond, B., Nix, R., Arana, N., Jacobs, J., and Talbot, W. S. (2005). erbb3 and erbb2 are essential for schwann cell migration and myelination in zebrafish. Curr Biol 15, 513-524.

Makinodan, M., Rosen, K., Ito, S., and Corfas, G. (2012). A critical period for social experience-dependent oligodendrocyte maturation and myelination. Science 337, 1357-1360.

Mangin, J.-M. M., Li, P., Scafidi, J., and Gallo, V. (2012). Experience-dependent regulation of NG2 progenitors in the developing barrel cortex. Nat Neurosci 15, 1192-1194.

Meijering, E., Dzyubachyk, O., and Smal, I. (2012). Methods for Cell and Particle Tracking. Methods Enzymol 504, 183-200.

Mensch, S., Baraban, M., Almeida, R., Czopka, T., Ausborn, J., El Manira, A., and Lyons, D. A. (2015). Synaptic vesicle release regulates myelin sheath number of individual oligodendrocytes in vivo. Nat. Neurosci. 18, 628-630.

Miller, R. (2002). Regulation of oligodendrocyte development in the vertebrate CNS. Prog. Neurobiol. 67, 451-467.

Monk, K. R., Naylor, S. G., Glenn, T. D., Mercurio, S., Perlin, J. R., Dominguez, C., Moens, C. B., and Talbot, W. S. (2009). A G protein-coupled receptor is essential for Schwann cells to initiate myelination. Science 325, 1402-1405.

Morris, A. D., Lewis, G. M., and Kucenas, S. (2017). Perineurial Glial Plasticity and the Role of TGF-β in the Development of the Blood-Nerve Barrier. J Neurosci 37, 4790-4807.

Moscou, M. J., and Bogdanove, A. J. (2009). A simple cipher governs DNA recognition by TAL effectors. Science 326, 1501.

Nakayama, T., Blitz, I. L., Fish, M. B., Odeleye, A. O., Manohar, S., Cho, K. W., and Grainger, R. M. (2014). Cas9-Based Genome Editing in Xenopus tropicalis. Methods Enzymol 546, 355.

Ongini, E., Dionisotti, S., Gessi, S., Irenius, E., and Fredholm, B. B. (1999). Comparison of CGS 15943, ZM 241385 and SCH 58261 as antagonists at human adenosine receptors. Naunyn-Schmiedeberg's Arch Pharmacol 359, 7-10.

Othman, T., Yan, H., and Rivkees, S. (2003). Oligodendrocytes express functional A1 adenosine receptors that stimulate cellular migration. Glia 44, 166-172.

Park, H.-C. C., Mehta, A., Richardson, J. S., and Appel, B. (2002). olig2 is required for zebrafish primary motor neuron and oligodendrocyte development. Dev. Biol. 248, 356-368.

Prendergast, A., Linbo, T. H., Swarts, T., Ungos, J. M., McGraw, H. F., Krispin, S., Weinstein, B. M., and Raible, D. W. (2012). The metalloproteinase inhibitor Reck is essential for zebrafish DRG development. Development 139, 1141-1152.

Rebola, N., Lujan, R., Cunha, R. A., and Mulle, C. (2008). Adenosine A2A receptors are essential for long-term potentiation of NMDA-EPSCs at hippocampal mossy fiber synapses. Neuron 57, 121-134.

Richardson, W. D., Smith, H. K., Sun, T., Pringle, N. P., Hall, A., and Woodruff, R. (2000). Oligodendrocyte lineage and the motor neuron connection. Glia 29, 136-142.

Rowitch, D. H. (2004). Glial specification in the vertebrate neural tube. Nat. Rev. Neurosci. 5, 409-419.

Saint-Amant, L., and Drapeau, P. (2001). Synchronization of an embryonic network of identified spinal interneurons solely by electrical coupling. Neuron 31, 1035-1046.

Sander, J. D., Cade, L., Khayter, C., Reyon, D., Peterson, R. T., Joung, J. K., and Yeh, J. R. (2011). Targeted gene disruption in somatic zebrafish cells using engineered TALENs. Nat Biotechnol 29, 697-698.

Searl, T. J., and Silinsky, E. M. (2012). Evidence for constitutively-active adenosine receptors at mammalian motor nerve endings. Eur. J. Pharmacol. 685, 38-41.

Sebastiao, A., and Ribeiro, J. (2015). Neuromodulation and metamodulation by adenosine: impact and subtleties upon synaptic plasticity regulation. Brain Res 1621, 102-113.

Shin, J., Park, H.-C. C., Topczewska, J. M., Mawdsley, D. J., and Appel, B. (2003). Neural cell fate analysis in zebrafish using olig2 BAC transgenics. Methods Cell Sci 25, 7-14.

Sievers, F., Wilm, A., Dineen, D., Gibson, T., Karplus, K., Li, W., Lopez, R., McWilliam, H., Remmert, M., Soding, J., et al. (2011). Fast, scalable generation of high-quality protein multiple sequence alignments using Clustal Omega. Mol Syst Biol 7, 539.

Simons, M., and Nave, K. (2016). Oligodendrocytes: myelination and axonal support. Cold Spring Harb Perspect Biol 8, a020479.

Smith, C., Morris, A., Welsh, T. W., and Kucenas, S. (2014). Contact-Mediated Inhibition Between Oligodendrocyte Progenitor Cells and Motor Exit Point Glia Establishes the Spinal Cord Transition Zone. Plos Biol 12.

Stevens, B., Porta, S., Haak, L., Gallo, V., and Fields, R. (2002). Adenosine A Neuron-Glial Transmitter Promoting Myelination in the CNS in Response to Action Potentials. Neuron 36, 855-868.

Tong, X., Li, X., Zhou, B., Shen, W., Zhang, Z., Xu, T., and Duan, S. (2009). Ca 2+ signaling evoked by activation of Na+ channels and Na+/Ca 2+ exchangers is required for GABA-induced NG2 cell migration. J Cell Biol 186, 113-128.

Truett, G., Heeger, P., Mynatt, R., Truett, A., Walker, J., and Warman, M. (2000). Preparation of PCR-quality mouse genomic DNA with hot sodium hydroxide and tris (Hot-SHOT). Biotechniques 29, 52, 54.

Vermeren, M., Maro, G. S., Bron, R., McGonnell, I. M., Charnay, P., Topilko, P., and Cohen, J. (2003). Integrity of developing spinal motor columns is regulated by neural crest derivatives at motor exit points. Neuron 37, 403-415.

Wei, W., Du, C., Lv, J., Zhao, G., Li, Z., Wu, Z., Haskó, G., and Xie, X. (2013).

Blocking A2B adenosine receptor alleviates pathogenesis of experimental autoimmune encephalomyelitis via inhibition of IL-6 production and Th17 differentiation. J Immunol 190, 138-146.

Xiao, L., Hu, C., Yang, W., Guo, D., Li, C., Shen, W., Liu, X., Aijun, H., Dan, W., and He, C. (2013). NMDA receptor couples Rac1-GEF Tiam1 to direct oligodendrocyte precursor cell migration. Glia 61, 2078-2099.

Yu, R. C., Power, J., Barnea, G., O'Donnell, S., Brown, H. E., Osborne, J., Axel, R., and Gogos, J. A. (2004). Spontaneous neural activity is required for the establishment and maintenance of the olfactory sensory map. Neuron 42, 553-566.

Zuchero, J. B., and Barres, B. A. (2015). Glia in mammalian development and disease. Development 142, 3805-3809.

What is claimed is:

1. A method for treating demyelination of a peripheral motor nerve in a subject with a disease, disorder, or injury associated with demyelination of a peripheral motor nerve, said method comprising stimulating oligodendrocyte progenitor cells (OPC) migration from the spinal cord of said subject to a peripheral motor nerve by administering to the subject a pharmaceutical composition comprising an effective amount of an inhibitor of adenosine A2a receptor (A2a AR) activity selected from the group consisting of CGS-15943 and SCH-58261, wherein when said OPCs migrate to the peripheral motor nerve said OPCs myelinate said peripheral motor nerve.

2. The method of claim 1, wherein the disease, disorder, or injury associated with demyelination of a peripheral motor nerve is selected from the group consisting of Guillain-Barre syndrome, chronic inflammatory demyelinating polyneuropathy (CIDP), anti-MAG peripheral neuropathy, Charcot-Marie-Tooth disease, Hereditary neuropathy with liability to pressure palsy, a copper deficiency associated condition, and progressive inflammatory neuropathy.

3. The method of claim 2, wherein said copper deficiency associated condition is selected from the group consisting of peripheral neuropathy, myelopathy, and optic neuropathy.

4. The method of claim 1, wherein a second inhibitor of A2a AR activity is administered.

5. The method of claim 1, wherein said pharmaceutical composition further comprises a pharmaceutically acceptable carrier.

6. The method of claim 1, wherein said inhibitor is administered at a dose ranging from about 0.001 mg/kg body weight to about 100 mg/kg body weight.

7. The method of claim 6, wherein said inhibitor is administered at a dose ranging from about 0.01 mg/kg body weight to about 10 mg/kg body weight.

8. The method of claim 1, wherein said inhibitor is administered as a unit dose ranging from about 0.1 mg to about 100 mg.

9. The method of claim 8, wherein said inhibitor is administered as a unit dose ranging from about 1.0 mg to about 10 mg.

* * * * *